US010357292B2

(12) United States Patent
Rains et al.

(10) Patent No.: US 10,357,292 B2
(45) Date of Patent: Jul. 23, 2019

(54) COMPOSITE INTERNAL FIXATORS

(71) Applicant: Smith & Nephew, Inc., Memphis, TN (US)

(72) Inventors: James K. Rains, Cordova, TN (US); Gene Edward Austin, Bartlett, TN (US); John Rose, Collierville, TN (US); Joseph Michael Ferrante, Barlett, TN (US); Darin S. Gerlach, Germantown, TN (US); Nathaniel Kelley Grusin, Germantown, TN (US); Sied W. Janna, Memphis, TN (US); Henry B. Faber, Memphis, TN (US); Mark S. Gosney, Cordova, TN (US); Darren James Wilson, York (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/296,762

(22) Filed: Oct. 18, 2016

(65) Prior Publication Data
US 2017/0035469 A1 Feb. 9, 2017

Related U.S. Application Data

(63) Continuation of application No. 13/124,555, filed as application No. PCT/US2009/060866 on Oct. 15, 2009, now Pat. No. 9,492,210.
(Continued)

(51) Int. Cl.
*A61B 17/72* (2006.01)
*A61B 17/80* (2006.01)
(Continued)

(52) U.S. Cl.
CPC .............. *A61B 17/72* (2013.01); *A61B 17/80* (2013.01); *A61B 90/39* (2016.02);
(Continued)

(58) Field of Classification Search
CPC ........ A61B 17/7283; A61B 17/72–748; A61B 19/54
(Continued)

(56) References Cited

U.S. PATENT DOCUMENTS 4,096,477 A 6/1978 Epstein et al.
4,281,664 A 8/1981 Duggan
(Continued)

FOREIGN PATENT DOCUMENTS

DE 202006009013 U1 8/2006
EP 62459 A1 10/1982
(Continued)

OTHER PUBLICATIONS

Authorized officer Jang, Ki Wan, International Search Report in PCT/US2009/060866, dated May 28, 2010, 3 pages.
(Continued)

*Primary Examiner* — Nicholas J Plionis

(57) ABSTRACT

A multi-layer, fiber-reinforced composite orthopedic fixation device having a design selected based on a desired characteristic of the orthopedic fixation device. The design may be selected according to a model of the device, the model defining design constraints, and the design may comprise a pattern of the fiber angle for each layer. The selection of a design may be analyzed using finite element analysis to determine whether the design will comprise the desired characteristic.

20 Claims, 21 Drawing Sheets

Related U.S. Application Data

(60) Provisional application No. 61/105,717, filed on Oct. 15, 2008, provisional application No. 61/180,403, filed on May 21, 2009.

(51) Int. Cl.
*A61B 90/00* (2016.01)
*A61B 17/00* (2006.01)

(52) U.S. Cl.
CPC ....... *A61B 17/7216* (2013.01); *A61B 17/7225* (2013.01); *A61B 17/7283* (2013.01); *A61B 2017/00022* (2013.01); *A61B 2017/00411* (2013.01); *A61B 2017/00415* (2013.01); *A61B 2017/00526* (2013.01); *A61B 2017/00734* (2013.01); *A61B 2017/00831* (2013.01); *A61B 2017/00955* (2013.01); *A61B 2090/0436* (2016.02); *A61B 2090/064* (2016.02)

(58) Field of Classification Search
USPC ...................................................... 606/62–68
See application file for complete search history.

(56) References Cited

U.S. PATENT DOCUMENTS

| | | |
|---|---|---|
| 4,338,926 A | 7/1982 | Kummer et al. |
| 4,361,153 A | 11/1982 | Slocum et al. |
| 4,403,606 A | 9/1983 | Woo et al. |
| 4,419,095 A | 12/1983 | Nebergall et al. |
| 4,512,038 A | 4/1985 | Alexander et al. |
| 4,513,743 A | 4/1985 | van Arragon et al. |
| 4,576,158 A | 3/1986 | Boland |
| 4,795,463 A | 1/1989 | Gerow |
| 4,808,186 A | 2/1989 | Smith |
| 4,860,331 A | 8/1989 | Williams et al. |
| 4,935,019 A | 6/1990 | Papp, Jr. |
| 4,952,928 A | 8/1990 | Carroll et al. |
| 4,960,655 A | 10/1990 | Hope et al. |
| 4,985,019 A | 1/1991 | Michelson |
| 5,009,664 A | 4/1991 | Sievers |
| 5,024,239 A | 6/1991 | Rosenstein |
| 5,064,439 A | 11/1991 | Chang et al. |
| 5,181,930 A | 1/1993 | Dumbleton et al. |
| 5,299,584 A | 4/1994 | Miyazaki et al. |
| 5,309,919 A | 5/1994 | Snell et al. |
| 5,330,477 A | 7/1994 | Crook |
| 5,337,747 A | 8/1994 | Neftel |
| 5,361,766 A | 11/1994 | Nichols et al. |
| 5,383,935 A | 1/1995 | Shirkhanzadeh |
| 5,397,365 A | 3/1995 | Trentacosta |
| 5,405,402 A | 4/1995 | Dye et al. |
| 5,423,334 A | 6/1995 | Jordan |
| 5,533,519 A | 7/1996 | Radke et al. |
| 5,571,202 A | 11/1996 | Mathys, Sr. et al. |
| 5,578,034 A | 11/1996 | Estes |
| 5,584,836 A | 12/1996 | Ballintyn et al. |
| 5,630,835 A | 5/1997 | Brownlee |
| 5,676,146 A | 10/1997 | Scarborough |
| 5,695,496 A | 12/1997 | Orsak et al. |
| 5,702,448 A | 12/1997 | Buechel et al. |
| 5,735,887 A | 4/1998 | Barreras, Sr. et al. |
| 5,776,194 A | 7/1998 | Mikol et al. |
| 5,792,076 A | 8/1998 | Orsak et al. |
| 5,833,603 A | 11/1998 | Kovacs et al. |
| 5,836,989 A | 11/1998 | Shelton |
| 5,873,843 A | 2/1999 | Draper |
| 5,904,708 A | 5/1999 | Goedeke |
| 6,206,881 B1 | 3/2001 | Frigg et al. |
| 6,245,109 B1 | 6/2001 | Mendes et al. |
| 6,269,148 B1 | 7/2001 | Jessop et al. |
| 6,299,649 B1 | 10/2001 | Chang et al. |
| 6,312,612 B1 | 11/2001 | Sherman et al. |
| 6,342,055 B1 | 1/2002 | Eisermann et al. |
| 6,447,448 B1 | 9/2002 | Ishikawa et al. |
| 6,461,359 B1 | 10/2002 | Tribus et al. |
| 6,529,127 B2 | 3/2003 | Townsend et al. |
| 6,583,630 B2 | 6/2003 | Mendes et al. |
| 6,610,096 B2 | 8/2003 | MacDonald |
| 6,632,563 B1 | 10/2003 | Krasnov et al. |
| 6,641,893 B1 | 11/2003 | Suresh et al. |
| 6,675,044 B2 | 1/2004 | Chen |
| 6,712,778 B1 | 3/2004 | Jeffcoat et al. |
| 6,738,671 B2 | 5/2004 | Christophersom et al. |
| 6,740,120 B1 | 5/2004 | Grimes |
| 6,764,446 B2 | 7/2004 | Wolinsky et al. |
| 6,766,200 B2 | 7/2004 | Cox |
| 6,790,372 B2 | 9/2004 | Roy et al. |
| 6,793,659 B2 | 9/2004 | Putnam |
| 6,819,247 B2 | 11/2004 | Birnbach et al. |
| 6,834,436 B2 | 12/2004 | Townsend et al. |
| 6,926,670 B2 | 8/2005 | Rich et al. |
| 6,939,299 B1 | 9/2005 | Petersen et al. |
| 6,968,743 B2 | 11/2005 | Rich et al. |
| 7,005,543 B2 | 2/2006 | Zhang |
| 7,027,871 B2 | 4/2006 | Burnes et al. |
| 7,034,694 B2 | 4/2006 | Yamaguchi et al. |
| 7,090,676 B2 | 8/2006 | Huebner et al. |
| 7,097,662 B2 | 8/2006 | Evans, III et al. |
| 7,151,914 B2 | 12/2006 | Brewer |
| 7,182,736 B2 | 2/2007 | Roy et al. |
| 7,189,238 B2 | 3/2007 | Lombardo et al. |
| 7,209,790 B2 | 4/2007 | Thompson et al. |
| 7,212,133 B2 | 5/2007 | Goetz et al. |
| 7,256,695 B2 | 8/2007 | Hamel et al. |
| 7,333,013 B2 | 2/2008 | Berger |
| 7,381,223 B2 | 6/2008 | Kovacevic |
| 7,474,223 B2 | 1/2009 | Nycz et al. |
| 7,559,951 B2 | 7/2009 | DiSilvestro et al. |
| 7,729,758 B2 | 6/2010 | Haller et al. |
| 8,007,450 B2 | 8/2011 | Williams |
| 9,492,210 B2 * | 11/2016 | Rains .................... A61B 17/72 |
| 2001/0021873 A1 | 9/2001 | Stinson |
| 2001/0034528 A1 | 10/2001 | Foerster et al. |
| 2001/0053912 A1 | 12/2001 | Frigg |
| 2002/0029041 A1 | 3/2002 | Hover et al. |
| 2002/0082683 A1 | 6/2002 | Stinson et al. |
| 2003/0040806 A1 | 2/2003 | MacDonald |
| 2003/0081732 A1 | 5/2003 | Broyles et al. |
| 2003/0136417 A1 | 7/2003 | Fonseca et al. |
| 2003/0139812 A1 | 7/2003 | Garcia et al. |
| 2004/0010313 A1 | 1/2004 | Aston et al. |
| 2004/0019356 A1 | 1/2004 | Fraser et al. |
| 2004/0059336 A1 | 3/2004 | Lombardo et al. |
| 2004/0077073 A1 | 4/2004 | Schindler et al. |
| 2004/0092818 A1 | 5/2004 | Weaver et al. |
| 2004/0113790 A1 | 6/2004 | Hamel et al. |
| 2004/0116837 A1 | 6/2004 | Yamaguchi et al. |
| 2004/0152972 A1 | 8/2004 | Hunter |
| 2004/0176815 A1 | 9/2004 | Janzig et al. |
| 2004/0204647 A1 | 10/2004 | Grupp et al. |
| 2004/0215195 A1 | 10/2004 | Shipp et al. |
| 2004/0220668 A1 | 11/2004 | Eisermann et al. |
| 2004/0243129 A1 | 12/2004 | Moumene et al. |
| 2004/0243138 A1 | 12/2004 | Cole |
| 2005/0010139 A1 | 1/2005 | Aminian et al. |
| 2005/0012617 A1 | 1/2005 | DiSilvestro et al. |
| 2005/0021029 A1 | 1/2005 | Trieu et al. |
| 2005/0055027 A1 | 3/2005 | Yeung et al. |
| 2005/0061673 A1 | 3/2005 | Presto Elgstoen et al. |
| 2005/0085812 A1 | 4/2005 | Sherman et al. |
| 2005/0099290 A1 | 5/2005 | Govari |
| 2005/0101833 A1 | 5/2005 | Hsu et al. |
| 2005/0131397 A1 | 6/2005 | Levin |
| 2005/0143823 A1 | 6/2005 | Boyd et al. |
| 2005/0187550 A1 | 8/2005 | Grusin |
| 2005/0187555 A1 | 8/2005 | Biedermann et al. |
| 2005/0234555 A1 | 10/2005 | Sutton et al. |
| 2005/0246020 A1 | 11/2005 | Southworth et al. |
| 2005/0247319 A1 | 11/2005 | Berger |
| 2005/0273106 A1 | 12/2005 | Oepen |
| 2005/0273170 A1 | 12/2005 | Navarro et al. |
| 2005/0288727 A1 | 12/2005 | Penner |
| 2006/0009656 A1 | 1/2006 | Zhang |

(56) References Cited

U.S. PATENT DOCUMENTS

| | | |
|---|---|---|
| 2006/0047283 A1 | 3/2006 | Evans, III et al. |
| 2006/0052782 A1 | 3/2006 | Morgan et al. |
| 2006/0058627 A1 | 3/2006 | Flaherty et al. |
| 2006/0069447 A1 | 3/2006 | DiSilvestro et al. |
| 2006/0072706 A1 | 4/2006 | Russell |
| 2006/0079900 A1 | 4/2006 | Mathieu et al. |
| 2006/0106400 A1* | 5/2006 | Fernandez ......... A61B 17/1703 606/97 |
| 2006/0111291 A1 | 5/2006 | DiMauro et al. |
| 2006/0129050 A1 | 6/2006 | Martinson et al. |
| 2006/0161159 A1 | 7/2006 | Dreyfuss et al. |
| 2006/0161168 A1 | 7/2006 | Matthys |
| 2006/0190080 A1 | 8/2006 | Danoff et al. |
| 2006/0200031 A1 | 9/2006 | White et al. |
| 2006/0232408 A1 | 10/2006 | Nycz et al. |
| 2006/0235410 A1 | 10/2006 | Ralph et al. |
| 2006/0260409 A1 | 11/2006 | Yane et al. |
| 2006/0264944 A1 | 11/2006 | Cole |
| 2006/0271112 A1 | 11/2006 | Martinson et al. |
| 2006/0271199 A1 | 11/2006 | Johnson |
| 2007/0010844 A1 | 1/2007 | Gong et al. |
| 2007/0049939 A1 | 3/2007 | Wallace et al. |
| 2007/0067882 A1 | 3/2007 | Atanasoska et al. |
| 2007/0078497 A1 | 4/2007 | Vandanacker |
| 2007/0089518 A1 | 4/2007 | Ericson et al. |
| 2007/0093836 A1 | 4/2007 | Derouet |
| 2007/0123938 A1 | 5/2007 | Haller et al. |
| 2007/0129769 A1 | 6/2007 | Bourget et al. |
| 2007/0173822 A1 | 7/2007 | Bruneau et al. |
| 2007/0185488 A1 | 8/2007 | Pohjonen et al. |
| 2007/0219639 A1 | 9/2007 | Otto et al. |
| 2007/0225219 A1* | 9/2007 | Boden ............... A61M 25/1011 424/400 |
| 2007/0246349 A1 | 10/2007 | Yamamoto et al. |
| 2007/0269016 A1 | 11/2007 | Mackey |
| 2007/0270691 A1 | 11/2007 | Bailey et al. |
| 2007/0270833 A1 | 11/2007 | Bonutti et al. |
| 2007/0270851 A1 | 11/2007 | Erickson et al. |
| 2007/0276383 A1 | 11/2007 | Rayhack |
| 2008/0086129 A1 | 4/2008 | Lindemann et al. |
| 2008/0097445 A1 | 4/2008 | Weinstein |
| 2008/0115686 A1 | 5/2008 | Crist et al. |
| 2008/0133022 A1 | 6/2008 | Caylor |
| 2008/0147098 A1* | 6/2008 | Trieu ............... A61B 17/8085 606/151 |
| 2008/0147125 A1 | 6/2008 | Colleran et al. |
| 2008/0154310 A1 | 6/2008 | White et al. |
| 2008/0161862 A1 | 7/2008 | Ensign |
| 2008/0177291 A1 | 7/2008 | Jensen et al. |
| 2008/0183221 A1 | 7/2008 | Burdulis |
| 2008/0195159 A1 | 8/2008 | Kloss et al. |
| 2008/0208516 A1 | 8/2008 | James |
| 2008/0221656 A1 | 9/2008 | Hartley et al. |
| 2008/0269744 A1* | 10/2008 | Kay ............... A61B 17/1725 606/62 |
| 2008/0300597 A1 | 12/2008 | Morgan et al. |
| 2009/0093819 A1 | 4/2009 | Joshi |
| 2009/0228007 A1 | 9/2009 | Justin et al. |
| 2010/0016985 A1 | 1/2010 | Rabiei |
| 2010/0152621 A1 | 6/2010 | Janna et al. |
| 2011/0087228 A1 | 4/2011 | Ferrante et al. |
| 2011/0152725 A1 | 6/2011 | Demir et al. |

FOREIGN PATENT DOCUMENTS

| | | |
|---|---|---|
| EP | 1099415 A1 | 5/2001 |
| EP | 1541095 A1 | 6/2005 |
| EP | 1570781 A1 | 9/2005 |
| EP | 1570782 A1 | 9/2005 |
| EP | 1622528 A1 | 2/2006 |
| EP | 1642550 A1 | 4/2006 |
| EP | 1660146 A1 | 5/2006 |
| EP | 1704893 A1 | 9/2006 |
| FR | 2822367 A1 | 9/2002 |
| GB | 2330078 A1 | 4/1999 |
| GB | 2405342 A1 | 3/2005 |
| JP | H05327180 | 9/1993 |
| WO | WO1985004234 A1 | 9/1985 |
| WO | WO1989007056 A1 | 8/1989 |
| WO | WO1990006720 A2 | 6/1990 |
| WO | WO1996009014 A1 | 3/1996 |
| WO | WO1996021397 A2 | 7/1996 |
| WO | WO1996026678 A1 | 9/1996 |
| WO | WO1996026678 A2 | 9/1996 |
| WO | WO1996029007 A1 | 9/1996 |
| WO | WO1997020512 A1 | 6/1997 |
| WO | WO1998041161 A1 | 9/1998 |
| WO | WO2000018317 A1 | 4/2000 |
| WO | WO2000019888 A1 | 4/2000 |
| WO | WO2000030534 A1 | 6/2000 |
| WO | WO2001019248 A1 | 3/2001 |
| WO | WO2002056763 A1 | 7/2002 |
| WO | WO2002058551 A1 | 8/2002 |
| WO | WO2003008570 A1 | 1/2003 |
| WO | WO2004052453 A1 | 6/2004 |
| WO | WO2004052456 A1 | 6/2004 |
| WO | WO2004069061 A1 | 8/2004 |
| WO | WO2005018684 A1 | 3/2005 |
| WO | WO2005018698 A1 | 3/2005 |
| WO | WO2005084544 A1 | 9/2005 |
| WO | WO2005104997 A1 | 11/2005 |
| WO | WO2005120203 A1 | 12/2005 |
| WO | WO2005120203 A2 | 12/2005 |
| WO | WO2006045607 A1 | 5/2006 |
| WO | WO2006052765 A1 | 5/2006 |
| WO | WO2006055547 A1 | 5/2006 |
| WO | WO2006089069 A1 | 8/2006 |
| WO | WO2006094273 A1 | 9/2006 |
| WO | WO2006113660 A1 | 10/2006 |
| WO | WO2006131302 A1 | 12/2006 |
| WO | WO2007009123 A1 | 1/2007 |
| WO | WO2007010671 A1 | 1/2007 |
| WO | WO2007025191 A1 | 3/2007 |
| WO | WO2007041265 A1 | 4/2007 |
| WO | WO2007069251 A1 | 6/2007 |
| WO | WO2007086832 A1 | 8/2007 |
| WO | WO2007101267 A1 | 9/2007 |
| WO | WO2007138062 A1 | 12/2007 |
| WO | WO2008022136 A2 | 2/2008 |
| WO | WO2008044011 A2 | 4/2008 |
| WO | WO2008105874 A1 | 9/2008 |
| WO | WO2008120203 A2 | 10/2008 |
| WO | WO2010045473 A2 | 4/2010 |
| WO | WO2011082152 A2 | 7/2011 |
| WO | WO2013012717 A2 | 1/2013 |
| WO | WO2013012727 A2 | 1/2013 |
| WO | WO2013012731 A2 | 1/2013 |

OTHER PUBLICATIONS

Fujihara, K. et al.; "Feasibility of Knitted Carbon/PEEK Composites for Orthopedic Bone Plates"; Biomaterials, vol. 25, Issue 17, Aug. 2004, pp. 3877-3885; available online Dec. 9, 2003. Copyright © 2003 Elsevier Ltd.

Fujihara, K. et al.; "Fibrous Composite Materials in Dentistry and Orthopaedics: Review and Applications"; Composites Science and Technology, vol. 64, Issue 6, May 2004, pp. 775-788; available online Oct. 20, 2003. Copyright © 2003 Elsevier Ltd.

Zheng-Ming, Huang et al.; "Stiffness and Strength Design of Composite Bone Plates"; Composites Science and Technology, vol. 65, No. 1, 2005; pp. 73-85; available online Aug. 19, 2004. Copyright © 2004 Elsevier Ltd.

Fujihara, K. et al.; "Performance Study of Braided Carbon/PEEK Composite Compression Bone Plates"; Biomaterials, 2003, vol. 24, No. 15 (JUL), pp. 2661-2667. Copyright © 2003 Elsevier, Ltd.

Roberts, J. C. Ecker et al.; "Design of Mechanically Compatible Fasteners for Human Mandible Reconstruction"; NASA Conference Publication 3189, vol. 1, pp. 86-95; Dec. 1992, Baltimore, MD.

Mason, JJ et al.; "An Evaluation Of The Use Of Infrared Heating For Contouring 30% Short Carbon-Fibre-Reinforced Peek"; Journal

(56) References Cited

OTHER PUBLICATIONS

Of Materials Science Materials In Medicine, 1992, vol. 3, pp. 88-94. Copyright © 1992 Chapman & Hall.
Reinhold, M. et al.; "Comparison of Two Novel Fluoroscopy-based Stereotactic Methods for Cervical Pedicle Screw Placement and Review of the Literature"; European Spine Journal 2008 vol. 17, pp. 564-575. Published online: Jan. 22, 2008. Copyright © 2008 Springer-Verlag.
Reinhold, M. et al.; "Cervical Pedicle Screw Placement: Feasibility and Accuracy of Two New Insertion Techniques Based on Morphometric Data"; European Spine Journal 2007 vol. 16, pp. 47-56. Published online: Apr. 21, 2006. Copyright © 2006 Springer-Verlag.
Aryan, Henry E. et al.; "Bioabsorbable Anterior Cervical Plating: Initial Multicenter Clinical and Radiographic Experience"; SPINE vol. 32, No. 10, pp. 1084-1088. Copyright © 2007 Lippincott Williams & Wilkins, Inc.
Fujihara, K. et al.; "Development of Braided Carbon/Peek Composite Bone Plates"; Advanced Composites Letters, vol. 10, 2001. Publisher: Adcotec, Ltd., Premier House, Suite 501, 77 Oxford Street, London W1R 1RB, U.K.
Claes, Lutz et al.; "A New Radiolucent System for Vertebral Body Replacement: Its Stability in Comparison to Other Systems" Journal of Biomedical Materials Research Applied Biomaterials, vol. 48, pp. 82-89. Copyright © 1999 John Wiley & Sons, Inc.
Kurtz, Steven M. et al.; "PEEK Biomaterials in Trauma, Orthopedic, and Spinal Implants"; Biomaterials, vol. 28, pp. 4845-4869. Available online Aug. 7, 2007. Copyright © 2007 Elsevier Ltd.
Schambron, Thomas et al.; "Effects of Environmental Ageing on the Static and Cyclic Bending Properties of Braided Carbon Fibre/PEEK Bone Plates"; Composites: Part B, vol. 39, pp. 1216-1220. Copyright © 2008 Elsevier Ltd.
Bakar, Abu M.S., et al.; "Mechanical Properties of Injection Molded Hydroxyapatite-polyetheretherketone Biocomposites"; Composites Science and Technology, vol. 63, pp. 421-425. Copyright © 2002 Elsevier Ltd.
Patel, Vikas et al.; "Failure Analysis of Absorbable Cervical Plates"; Proceedings of the NASS 23rd Annual Meeting/The Spine Journal, vol. 8, p. 84S, Oct. 17, 2008.
Ramakrishna, Seeram et al.; "An Introduction To Biocomposites: Series on Biomaterials and Bioengineering" vol. 1, 1 Page. Copyright © 2004 Imperial College Press, 57 Shelton Street, Covent Garden, London WC2H 9HE, 2004.
Liu, D. et al , "Behavior of Quasi-three-dimensional Woven Composites"; Proceedings of the American Society for Composites Twenty-Third Technical Conference, Sep. 2008, Memphis, TN, USA. Copyright © 2008 DEStech Publications, Inc., Lancaster, Pennsylvania. (13 Pages).
Blom, A.W. et al., "Design and Manufacture of a Composite Cylinder with Circumferentially Varying Stiffness"; Proceedings of the American Society for Composites Twenty-Third Technical Conference, Sep. 2008, Memphis, TN, USA. Copyright © 2008 DEStech Publications, Inc., Lancaster, Pennsylvania. (20 Pages).
Pereira, T. et al.; "Development of Multifunctional Structural Composites for Energy Harvesting"; Proceedings of the American Society for Composites Twenty-Third Technical Conference, Sep. 2008, Memphis, TN, USA. Copyright © 2008 DEStech Publications, Inc., Lancaster, Pennsylvania. (9 Pages).
Office Action for Chinese Application No. 200980150422.4, dated Mar. 25, 2013.
Second Office Action Chinese Application No. 200980150422.4 dated Jan. 26, 2014.
Extended European Search Report for European Application No. 09821263.2, dated Apr. 24, 2014.
International Search Report and Written Opinion for International Application PCT/US2012/046681 dated Jan. 22, 2013, 11 pages.
International Search Report and Written Opinion for International Application PCT/US2012/046694 dated Jan. 28, 2013, 11 pages.
International Search Report and Written Opinion for International Application PCT/US2012/046659 dated Jan. 29, 2013, 10 pages.
Patent Examination Report No. 1 for Australian Application 2009305693, dated Oct. 7, 2014.
Chinese Office Action for Application No. 200980150422.4, dated Jan. 26, 2014.
Third Office Action for Chinese Application No. 200980150422.4, dated Jul. 25, 2014.
Fourth Chinese Office Action for Application No. 200980150422.4, dated Mar. 16, 2015.
Fifth Chinese Office Action for Application No. 200980150422.4, dated Nov. 5, 2015.
Communication Pursuant to Article 94(3) EPC for European Application No. 09821263.2, dated Feb. 22, 2016.
Examination Report for Indian Patent Application No. 2764/DELNP/2011 dated Jun. 7, 2018.

* cited by examiner

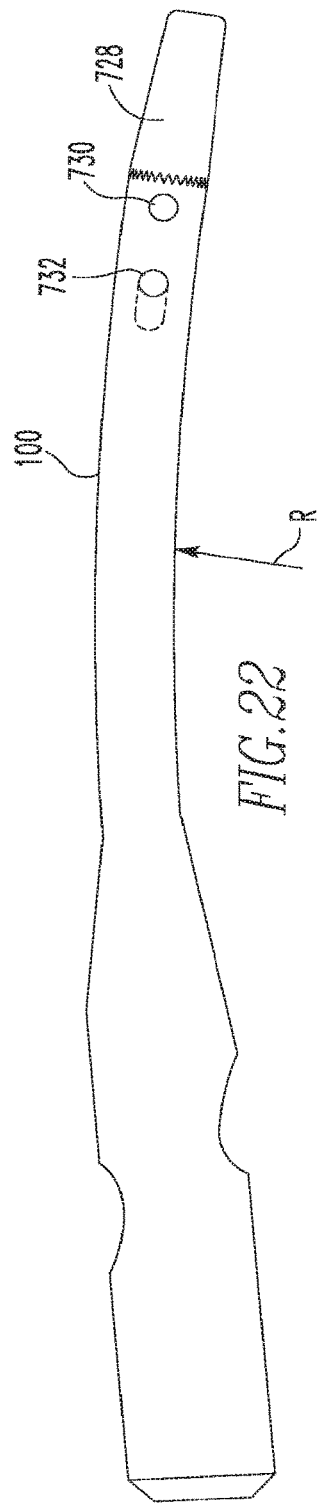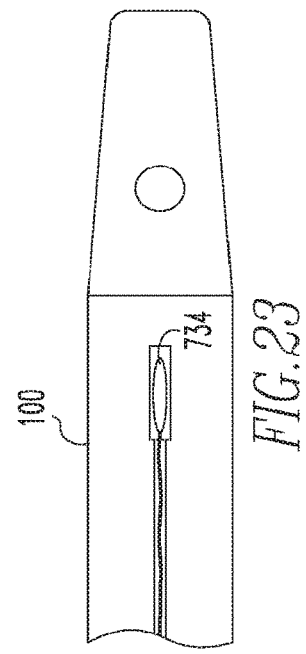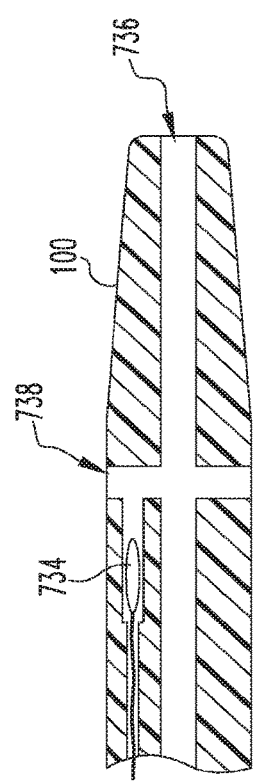

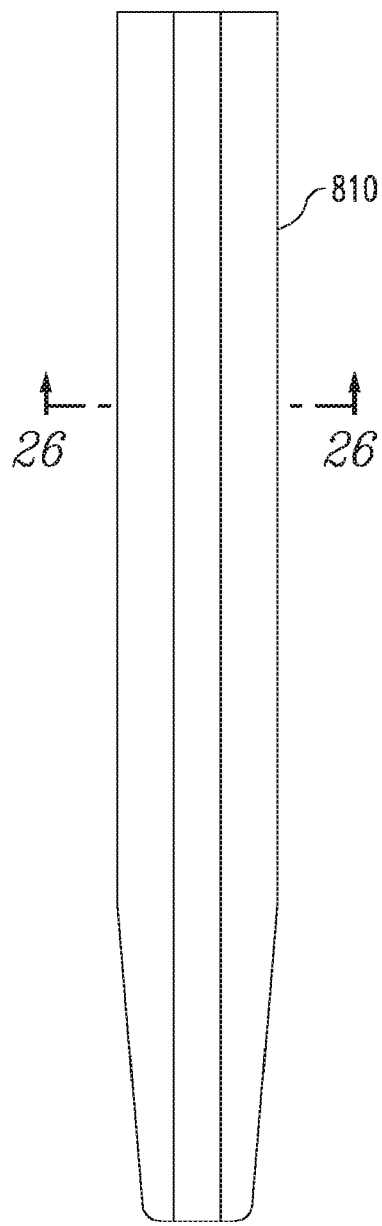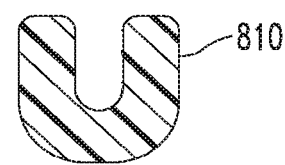
FIG.25
FIG.26

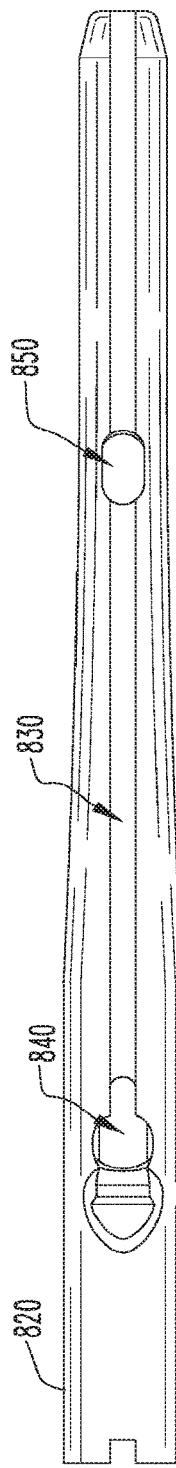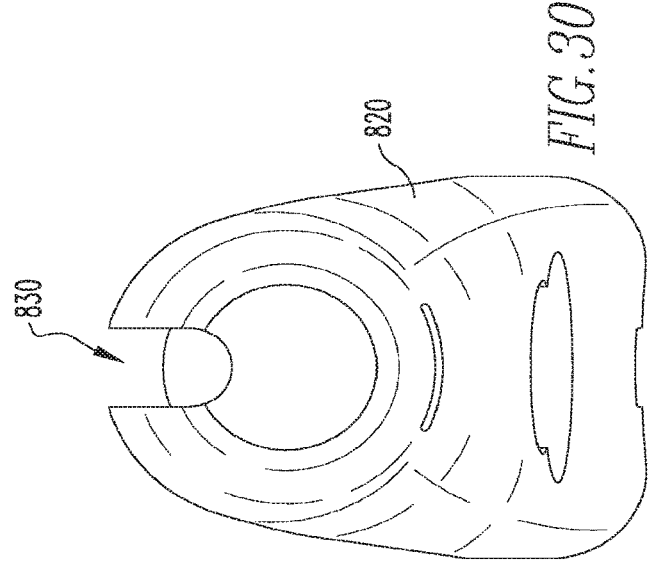

COMPOSITE INTERNAL FIXATORS

CROSS-REFERENCE TO RELATED APPLICATIONS

This application is a continuation of U.S. patent application Ser. No. 13/124,555, which is a national phase entry of PCT Application PCT/US2009/060866 and has a § 371 date of Nov. 21, 2011, now allowed, which claims the benefit of U.S. Provisional Application No. 61/105,717, filed Oct. 15, 2008, and U.S. Provisional Application No. 61/180,403, filed May 21, 2009. The disclosure of each application is incorporated by reference in its entirety.

BACKGROUND OF THE INVENTION

The present invention relates generally to orthopedic instrumentation and more specifically to internal fixation devices.

Orthopaedic fixation devices may be used, for example, to stabilize an injury, to support a bone fracture, to fuse a joint, or to correct a deformity. The orthopaedic fixation device may be attached permanently or temporarily, and may be attached to the bone at various locations, including implanted within a canal or other cavity of the bone, implanted beneath soft tissue and attached to an exterior surface of the bone, or disposed externally and attached by fasteners, such as screws, pins, and/or wires. Some orthopaedic fixation devices allow the position and/or orientation of two or more bone pieces, or two or more bones, to be adjusted relative to one another. Orthopaedic fixation devices are generally machined or molded from isotropic materials, such as metals, including titanium, titanium alloys, stainless steel, cobalt-chromium alloys, and tantalum.

Although metal implants have been used for over a century, some problems still remain. For example, there is a stiffness mismatch between a metal implant and bone. This sometimes leads to stress shielding and bone loss. Additionally, many patients are allergic to metallic implants. Finally, some metals have a significant acquisition lead time, which may disrupt manufacturing operations.

It is often necessary to place an orthopaedic fixation device relative to bone. Currently, there are two main techniques for obtaining correct orthopaedic fixation device depth within an intramedullary canal of a bone. The first and oldest is the surgeon using radiography to visually align the hole in the orthopaedic fixation device with the femoral head and neck. There is difficulty in identifying the axis of the hole in the orthopaedic fixation device with which to align with the femoral head and neck. The second and newer method is the use of alignment arms/jigs that are attached to a drill guide. A C-arm is used to achieve a radiographic view of the implant and drill guide being placed in the bone. The alignment arm is attached to the drill guide and extends out on the anterior side of the patient. The arm contains radio-opaque markers that are visible on the radiograph. The marker shows the projection of the fastener that is to go through the orthopaedic fixation device and into the femoral head, and the surgeon uses the projection to align the implant with the femoral head.

To obtain version this is normally performed by the surgeon using a radiograph to visually determine the correct rotation of the orthopaedic fixation device relative the femoral head and neck. In a medial-lateral view, the surgeon attempts to align the screw hole or nail profile with the femoral neck and head. Another method to attain appropriate version is with use of a drill guide that contains a set of plates or a metal wire imbedded in it that the user aligns with the femoral head and neck using radiography.

SUMMARY

According to one aspect of the invention, there is provided an orthopaedic fixation device, for example, an intramedullary nail or a plate, for use in supporting a bone or bone fragments, includes multiple layers of a biocompatible plastic and a reinforcing fiber, such as carbon fiber, to provide a laminated composite design. The design is selected to provide desired performance characteristics by selective orientation of the fibers within each layer. For example, the compression stiffness, bending stiffness, including cantilever bending stiffness, and torsion stiffness of the device can be controlled by the number and orientation of the plastic/fiber layers of the device. The device can be designed by a system that is operable to select a design from among predefined designs associated with a model of the device. The system analyzes the design to determine whether the design will produce an orthopaedic fixation device that satisfies the desired performance characteristics, and outputs the design if the desired performance characteristics are satisfied by the design. In use, the system can receive inputs from a user, such as desired performance values, including force, deflection, and/or stiffness values. Additionally or alternatively, the system can receive inputs including selected characteristics that describe the application and/or patient, such as pediatric, geriatric, or a mineral density of the bone to be secured, and the system determines performance values for the device based on the characteristics and/or the other inputs.

In one embodiment, there is provided a method of designing a laminated composite article comprising receiving, in a computer system, information regarding a desired characteristic of the article, selecting a model of the article based on the information, selecting a multi-layer, fiber-reinforced composite design of the article from a group of laminated composite designs associated with the model, comparing results of a finite element analysis of the selected design to the desired characteristic, and outputting the selected design when the comparison indicates that the article will exhibit the desired characteristic.

In another embodiment, the desired characteristic includes one of a compression stiffness, a bending stiffness, a torsion stiffness, specific patient information, generic patient information, and information regarding an isotropic article.

In yet another embodiment, there is provided a method of selecting a model of the article comprises selecting a model from a library of models.

In still another embodiment, the group of laminated composite designs comprises designs comprising fiber reinforced composite layers, each layer having a predetermined fiber angle orientation, the fiber angle orientations of the layers being symmetric about a middle of the layers of the design.

In another embodiment, the model comprises information regarding exterior and interior dimensions of the article.

In yet another embodiment, the designs are associated with a model based on a difference between an exterior dimension and an interior dimension of the model being less than a sum of the thicknesses of the layers of the design.

In still another embodiment, the selected design comprises instructions for manufacture of the laminated composite article.

In another embodiment, the instructions, when executed produce an orthopaedic fixation device suitable for implantation in a human patient.

In another aspect of the invention, there is provided an internal fixator for spanning a fracture, the internal fixator having a plurality of layers, each layer of the plurality of layers including a thermoplastic component and a fiber component and each layer of the plurality of layers having a selected fiber angle pattern, the selected fiber angle patterns being arranged symmetrically from a first layer to a last layer, and the symmetrical arrangement of fiber angle patterns including at least two layers having generally opposing fiber angle patterns.

In one embodiment of the invention, the internal fixator is one of an intramedullary nail and a bone plate.

In another embodiment, for each layer, the fibers of a layer are generally parallel.

In yet another embodiment, the invention also includes an aperture formed through the internal fixator for receiving a fastener.

In still another embodiment, a sleeve disposed in the aperture, the sleeve configured to receive the fastener therein.

In another embodiment, the invention includes an exterior coating of a thermoplastic material with substantially no fiber component.

In yet another embodiment, the internal fixator is an intramedullary nail, the intramedullary nail comprising a head, a shaft, and a transition region between the head and the shaft.

In still another embodiment the head comprises a greater number of layers than a number of layers of the shaft.

In another embodiment, selected fiber angle patterns of the layers are selected such that the device exhibits a selected stiffness characteristic.

In yet another aspect of the invention, there is provided a method of making a system for designing a laminated composite article comprising creating a library of models, the models defining exterior dimensions of the article, creating a library of laminated composite article designs, each design being associated with at least one model, and each design comprising a multi-layer construction of the article, each layer including a including information regarding a fiber angle for fibers of the layer, coding a selection engine configured to select a design from the library of designs based on a selected characteristic of the laminated composite article and for outputting a selected design, and coding a finite element analysis engine configured to determine that analysis of the selected design corresponds to the selected characteristic.

In one embodiment, creating a library of models comprises storing exterior dimensions of an intramedullary nail and storing a minimum diameter of a central cavity.

In another embodiment, associating a design with a model based on a determination that a sum of thickness of the layers of the design is less than a difference between the minimum diameter of the central cavity and a stored outer diameter associated with the model.

In yet another embodiment, the selection engine is operable to sequentially select a design associated with the model in an order according to increasing layer number.

In another embodiment, the finite element analysis engine is configured to determine whether the selected design will provide at least one of desired compression stiffness, a desired bending stiffness, and a desired torsion stiffness.

In yet another embodiment, configuring the system to output the selected design when the finite element analysis engine determines that the selected design corresponds to the selected characteristic.

In still another embodiment, configuring the system to select a different design when the finite element analysis engine determines that the selected design does not correspond to the selected characteristic.

In another embodiment, coding the finite element analysis engine comprises validating that the finite element analysis engine generates theoretical test results for designs that are similar to physical test results of the designs.

In yet another embodiment, coding the finite element analysis engine further comprises adjusting a parameter of the finite element analysis engine if the finite element analysis engine does not generate theoretical test results for designs that are similar to physical test results for the designs.

In still another aspect of the invention, there is provided a system for designing a laminated composite article comprising an input device configure to receive information regarding the laminated composite article, at least one storage device storing a plurality of models and storing a plurality of designs of laminated composite articles, each design associated with at least one model, a selection engine for selecting a design from the plurality of designs according to the model, a finite element analysis engine for generating analysis results for the selected design, and an output device for outputting the selected design.

In one embodiment, the system is configured to determine whether the analysis results are similar to the received information.

In another embodiment, the system is configured to output the selected design if the analysis results are determined to be similar to the received information.

In yet another embodiment, the selection engine is configured to select a design in an order according to increasing layer number.

In still another embodiment, the information relates to at least one of a compression stiffness, a bending stiffness, a torsion stiffness, specific patient information, generic patient information, and information regarding a an isotropic article.

In another embodiment, the specific patient information includes at least one of information regarding a patient's age and information regarding a bone mineral density of a patient's bone.

In yet another embodiment, the generic patient information includes at least one of information regarding an age group, information regarding a patient's activity level, and information regarding a bone quality of a patient's bone.

The details of one or more implementations are set forth in the accompanying drawings and the description below. Other features will be apparent from the description and drawings, and from the claims.

DESCRIPTION OF THE DRAWINGS

FIG. 22 illustrates an intramedullary nail in a seventh embodiment.

FIG. 23 illustrates an intramedullary nail in an eighth embodiment.

FIG. 24 illustrates a sectional side view of an intramedullary nail in a ninth embodiment.

FIG. 25 illustrates the intramedullary nail in a tenth embodiment.

FIG. 26 illustrates the intramedullary nail of FIG. 25 in a sectional view.

FIGS. 27-30 illustrate the intramedullary nail in an eleventh embodiment.

DETAILED DESCRIPTION

Figure 1:
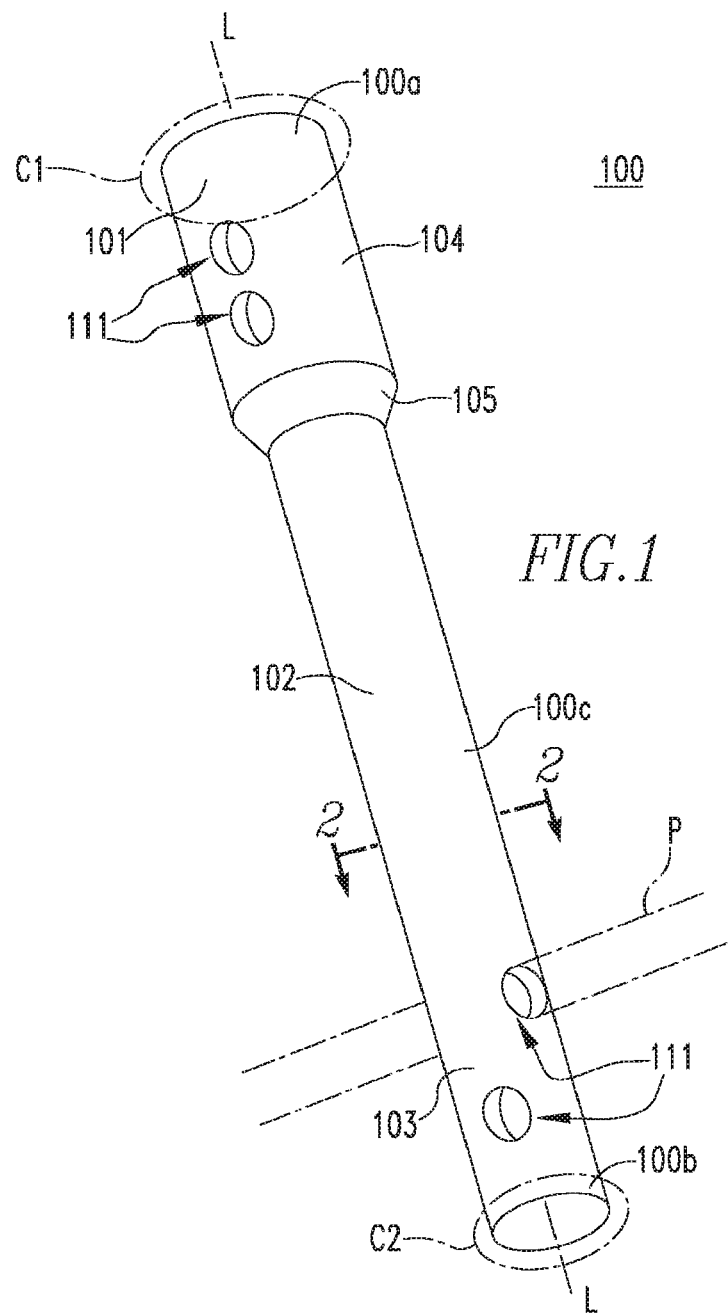
FIG. 1 is a perspective view of an orthopaedic fixation device.
Figure 2:
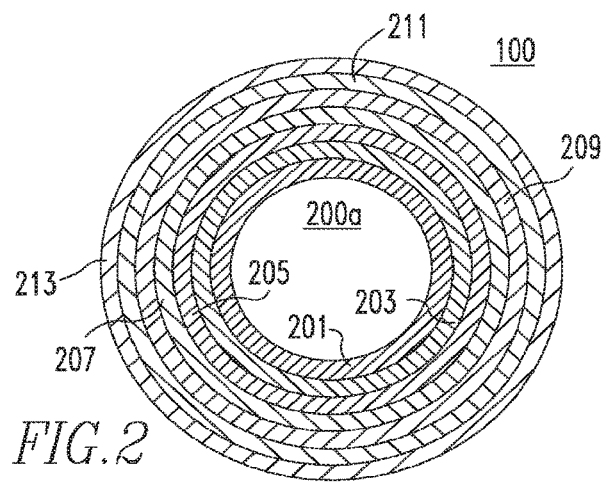
FIG. 2 is a cross-sectional view of the orthopaedic fixation device taken along line 2-2 of FIG. 1.
Figure 3:
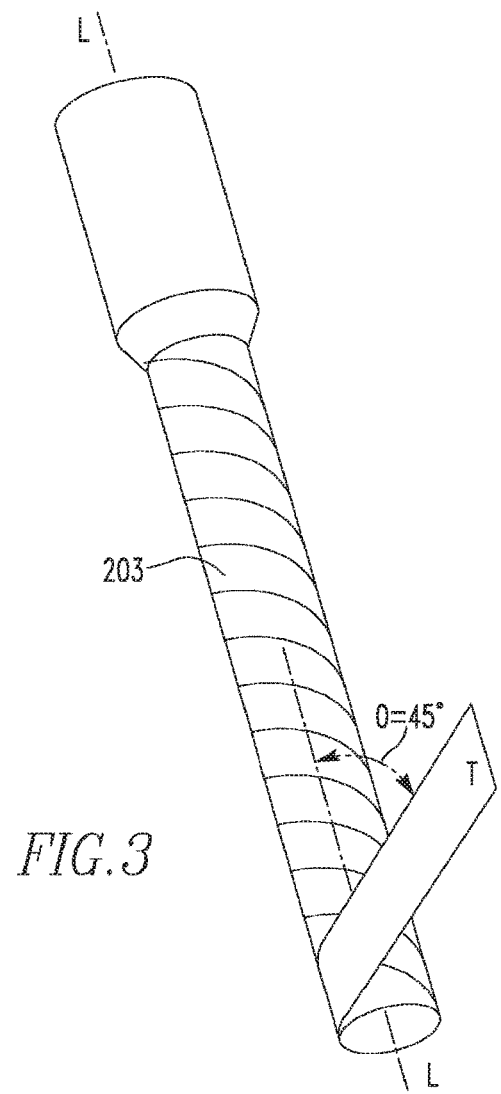
FIG. 3 is perspective view of an orthopaedic fixation device in construction.

Referring to FIGS. 1, 2 and 3, an intramedullary nail 100 includes a shaft 102 and a head 104. The shaft 102 defines apertures 111 for receiving screws, or other fasteners (not shown), and the head 104 defines apertures 111 for receiving pin P, screws, or other fasteners (not shown) for securing the intramedullary nail 100 within the intramedullary canal of a long bone. The fasteners may be made from metal, polymer, or a composite material.

The nail 100 is constructed of a plurality of layers 201-213 of a composite material, such as a polyetheretherketone (PEEK) and carbon fiber composite. The composite material can be a continuous fiber-reinforced material, such as a sheet, tape, or tow, in which the carbon fibers are generally aligned in parallel with the length dimensions of the fibers oriented in the length dimension of the sheet, tape, or tow. The layers have a generally uniform thickness in the range of 0.01 millimeters to 4 millimeters, with some implementations having a thickness of 0.14 millimeters±0.1 millimeters. The fibers of each layer are generally parallel and continuous, such that for each layer, all, or substantially all, of the fibers have a common angular orientation relative to a longitudinal axis L-L of the nail 100. For example, a first layer of the composite material can have fibers oriented generally across the length dimension at approximately ninety degrees to the longitudinal axis L-L. Another layer disposed above or below the first layer (or inside or outside of the first layer) can have fibers oriented at a five degree angle, or another selected angle, relative to the longitudinal axis L-L. In some embodiments, the first layer and/or the last layer may be made from virgin PEEK (i.e., PEEK without reinforcement).

Because the fibers of the composite material exhibit different mechanical characteristics in response to different forces relative to their longitudinal axis, and because the fibers of each layer are generally parallel and continuous, the affect of each layer on the mechanical characteristics of the nail 100 in response to different forces is determined by the relative orientation of the fibers to the longitudinal axis L-L of the nail 100. In many circumstances, the nail 100 benefits from having at least one layer having fibers oriented across the longitudinal axis L-L and at least one layer having fiber orientations generally along the longitudinal axis L-L. Furthermore, the orientation of the fibers of each layer of the nail 100 can be selected such that the nail 100 exhibits selected characteristics in response to various forces. For example, the nail 100 may exhibit selected stiffness characteristics in response to compression, bending, and torsion forces by selection of the fiber orientations of each layer thereof based on specific characteristics of the material.

The nail 100 includes a first end 100a, a second opposing end 100b, and a medial portion 100c extending between the first end 100a and the second end 100b. A first section 101 includes the first end 100a and has a first circumference C1. A second section 103 has a second circumference C2 and includes the second end 100b. Each of the first section 101 and the second section 103 has one or more apertures 111 formed therethrough for receiving a pin P, or other fastener, such as a screw, bolt, or rod (not shown), for connecting the nail 100 to bone. The nail 100 has a longitudinal axis L-L, and a circumference profile along the longitudinal axis L-L adapted for implantation within a canal of a bone, such as a femoral canal, a tibial canal, a humeral canal, or a clavical canal. As illustrated, the first section 101 has a first circumference C1, and the second section 103 has a second, smaller circumference C2. A transition section 105 has a decreasing circumference along the longitudinal axis L-L from the first circumference C1 to the second circumference C2 in the direction from the first end 100a towards the second end 100b. In some implementations, the first circumference C1 can be approximately 13 millimeters, and the second circumference C2 can be selected to approximately match the size of the canal of the bone into which the nail 100 is inserted. The transition section 105 can have a constant slope between the first section 101 and the second section 103, or can have a varying slope to achieve a rounded transition. It is possible that the second circumference C2 is approximately equal to the first circumference C1, and therefore, the transition section 105 can be omitted.

If a central cavity or cannulation 200a is desired, the nail 100 is formed, for example, by wrapping a pre-impregnated PEEK carbon-fiber tow around a mandrel to form a layer. After the nail 100 is formed, the mandrel is removed and the cavity 200a remains, and extends along a majority of the longitudinal axis L-L from the first end 100a toward the second end 100*b*. Alternatively, however, the nail can include a solid center. To form a solid nail, the mandrel remains within the layers, or can be replaced with another material, such as a biocompatible plastic material. Furthermore, the mandrel can be formed from a material that is dissolved and/or absorbed by the patient. For example, the mandrel may be absorbed such that the nail is solid when implanted and a cavity develops after implantation.

The mandrel can be selected such that it has an exterior dimension that approximately equals a desired interior dimension of the nail. Furthermore, the shape of the mandrel may be selected to provide a nail having a similar shape. For example, the mandrel may be cylindrical, and may have a circular, trapezoidal, oval, or other cross-sectional shape in order to provide a nail having such shapes. Additionally, the mandrel can include two or more portions having different shapes, such as a circular cylinder portion associated with the shaft and a rectangular cylinder portion associated with the head. In some implementations, a circular cylinder portion of the mandrel is associated with the shaft 102 of the nail 100 and a trapezoidal cylinder portion is associated with the head 104 of the nail 100.

During wrapping, the fibers can be routed around the apertures 111, such as by routing the tow around guide members disposed in the locations where the apertures 111 will be formed. By routing the fibers around the apertures 111, the need to subsequently remove pieces of the composite material to form the apertures 111 in the nail 100 can be avoided. Furthermore, forming the apertures 111 using the guide members can produce a smooth bore through the nail 100, and can avoid breaking the carbon fibers. Optionally, the apertures can be formed using guide members that are larger than the desired aperture size, and a sleeve or other reinforcing or protective member can be installed within the aperture formed by the guide member to create the apertures 111 of a desired size for receiving a pin P of corresponding size. Such a sleeve or reinforcing member can reduce damage to the composite material in an area near the apertures.

Subsequent layers can be added by wrapping the pre-impregnated carbon-fiber tow around the previous layer. When the layer wrapping is complete, the mandrel and other guides can be removed. Where a tow, tape, or ribbon is used, and as discussed above, the carbon fibers are disposed within the layer with a length of each fiber generally parallel to the length dimension of the tow. Thus, if a layer with a ninety degree fiber orientation is desired, the tow can be wrapped around the mandrel (and previous layer, if any are present) at approximately ninety degrees to the longitudinal axis L-L.

The nail 100 is adapted to be secured to different bones, or to different bone portions, via bone pins or screws (not shown) disposed in apertures 111. As such, the medial portion 100*c*, which includes the transition section 105, can be described as a working portion of the nail 100 that experiences compression, bending forces, and torsion that are applied to the different bones or different bone portions. For example, in a fracture-securing application, the nail 100 can support portions of a bone on opposite sides of a fracture, and can transfer a force applied to one bone portion to the other bone portion while generally maintaining the positions of the bone portions relative to one another. However, some relative movement between the bones or bone portions may be desired, or it may be desired that some portion of the forces be borne by the bone across the fracture site, during and/or after healing. Accordingly, the physical properties of the nail 100, at least in the medial portion 100*c*, can be selected such that the nail 100 exhibits acceptable bending, twisting, and compression deflection in response to anticipated bending, twisting, and compression forces associated with a selected application.

In some implementations, the first section 101 is formed without carbon fiber composite layers, at least in a proximal portion thereof, and the circumference C1 includes a molded structure formed of the thermoplastic material. In other implementations, the first section 101 includes multiple carbon fiber reinforced composite layers including the same layers that are included in the second section 103 having the second circumference, and some additional layers or thermoplastic material. For example, additional layers of the carbon fiber reinforced composite, such as layers having fibers oriented at 90 degrees to the longitudinal axis L-L, can be added to create the transition section 105 and the first section 101 having the first circumference C1. Alternatively, thermoplastic material can be added to the outer layer of the multiple carbon fiber reinforced composite layers to create the first section having the circumference C1 and the transition section 105. Additionally, as discussed above, the mandrel may include different portions associated with the first section 101, the second section 103, and the transition section 105 such that application of layers over the mandrel results in the desired exterior surface dimensions and shapes of the nail 100. A sleeve may be inserted within the central cavity 200*a* to provide a cannulation of uniform dimension, or of dimensions or shapes different from the dimensions or shape of the mandrel.

Such an outer layer of thermoplastic material, or other outer coating of material can be included not only to obtain a desired outer dimension, but can also be included to provide a desired texture or other property over the entire exterior surface, or over portions thereof. For example, a layer of biocompatible thermoplastic material can be included to provide a smooth exterior surface, which can aid in inhibiting growth of bacteria colonies. Furthermore, the coating material can be selected such that allergic reactions, or other undesired reactions, can be reduced or eliminated. Additionally, an outer layer and/or an inner layer of thermoplastic material, such as PEEK, reduces carbon fiber debris that can be created or released by interaction between an instrument, such as a drill, with the nail 100 during implantation. Debris can also be created or released after implantation by interaction between a bone pin or other component during use. An outer layer and/or and inner layer of thermoplastic material can inhibit escape of detached pieces.

The outer and/or inner layers of thermoplastic material can be formed by wrapping a tow of PEEK without fiber reinforcement. For example, an inner layer can be formed by first wrapping a tow of PEEK without fiber reinforcement around the mandrel. An outer layer can be formed by wrapping a tow of PEEK without fiber reinforcement around the outside of a carbon fiber reinforced layer. Alternatively, a tube or sleeve of thermoplastic material can be applied over the mandrel and/or over a last carbon fiber reinforced layer. Other techniques, such as printing or molding can also be used. Additionally, the nail 100 including such an inner and/or outer layer of thermoplastic material can be treated, such as in an autoclave, to consolidate the layers.

In one particular embodiment, a cylindrical mandrel is provided. The mandrel may be cannulated. The mandrel may have two or more radial through holes spaced apart from each end. Multiple layers of braided sleeves are placed over the mandrel. More layers may be placed on one end of the composite than the other for thickness. The braid is separated and pins are placed through the through holes in the mandrel for fastener holes in the intramedullary nail. The composite is autoclaved to consolidate the layers, and the pins are removed to provide through holes in the intramedullary nail. The mandrel thereafter may be removed.

An additional or alternative coating layer can be added to provide other desired characteristics. For example, non-metallic orthopedic devices can benefit from a coating to provide scratch resistance in order to protect the device from mechanical abrasion experienced during the surgical implantation procedure. The thickness of a scratch-resistant coating is about 2±0.5 µm. A scratch-resistant coating can be applied, e.g., by plasma immersion ion processing (PIP) techniques, physical vapor deposition (PVD), chemical vapor deposition (CVD), by dipping, or by spin coating.

The coating can be formed of diamond-like-carbon (DLC), which offers many of the properties of diamond, producing a lubricous, wear-resistant chemical barrier suitable for long term implantation. DLC film is deposited by starting with a carbon-containing gas such as acetylene to provide carbon atoms to deposit onto the substrate. The mechanical properties of the coating can be tailored to the requirements of the device by simply changing the deposition conditions. Particularly, a scratch-resistant layer can be precipitated through plasma polymerization to produce a thin, highly cross-linked layer. Examples include tetraethylorthosilicate and hexamethyldisiloxane.

Adding scratch-resistant properties in the nail 100 can be achieved by adding fillers during a molding operation. The size and concentration, known as loading, of the fillers used to reinforce the composite affect the final properties of the device. Micron-size particles are used to increase filler content while retaining processability, and nanofillers are incorporated to increase wear resistance. Nanofillers are well suited for use as fillers in the composite devices described herein because they will not compromise the volume fraction of the carbon fibers, and thus will not compromise flexural strength of the device. Biocompatible fillers include, but are not limited to, hydroxyapatite and silicon carbide.

To protect the carbon fibers in a surface layer of the device from mechanical abrasion, a PEEK coating or an over-mold "skin" of PEEK material can be applied. PEEK coatings have excellent substrate adhesion, and do not require a primer during the coating process. Additionally, a PEEK coating can be applied in a thin layer, which contributes to low manufacturing cost. Flame spraying and printing PEEK can be used to apply such a PEEK over-mold. An amorphous PEEK coating can be obtained by these techniques, and can be annealed to produce a more wear resistant semi-crystalline structure, if desired. Further, overmolding may prevent fluid from contacting the carbon fibers, which may affect stiffness of the construct.

Mechanically-induced damage can be reduced by modifying the surface topography of the device or cross-sectional geometry of the apertures, such that it is difficult to skive the drill across the surface during targeting of the apertures. The surface could be machined by grit/sand blasting, and a chamfer or bushing located in an aperture could be used to facilitate the location of the drill.

With reference to FIGS. 2 and 3, a cross-sectional view taken across the longitudinal axis L-L at the medial portion 100c illustrates a first layer 201 that defines the hollow central cavity 200a. The length dimensions of the fibers of the first layer 201 are oriented at approximately ninety degrees to the length dimension L. That is to say, the fibers wrap around the length dimension generally perpendicularly. A second layer 203 overlays the first layer 201 and can have a different fiber orientation than the fiber orientation of the first layer 201. For example, a tow T having fibers oriented in length dimension of the tow T is wrapped around the first layer 201 such that the longitudinal axis of the fibers of the second layer 203 are oriented at approximately positive forty-five degrees relative to the longitudinal axis L-L of the nail 100, where the proximal direction in the length dimension L is equal to zero degrees. A third layer 205 overlays the second layer 203 and includes fibers whose length dimensions are oriented at approximately negative forty-five degrees relative to the longitudinal axis L-L. Thus, the orientation of the fibers of the third layer 205 generally opposes, i.e., is approximately perpendicular to, the orientation of the fibers of the second layer 203.

A fourth layer 207 overlays the third layer 205 and includes fibers whose length dimensions are oriented generally along the longitudinal axis L-L. If the nail 100 is formed by wrapping a pre-impregnated carbon fiber reinforced tow T, the fourth layer 207 can include fibers whose length dimensions are oriented at positive or negative five degrees from the longitudinal axis L-L. Thus, the orientation of the fibers of the fourth layer 207 generally opposes the orientation of the fibers of the first layer 201. Alternatively, including implementations where the carbon fiber reinforced tow T is used, a layer that includes fibers oriented generally along the longitudinal axis L-L can be oriented at approximately zero degrees, i.e., parallel to the longitudinal axis L-L.

A fifth layer 209 overlays the fourth layer 207 and includes fibers oriented at approximately negative forty-five degrees relative to the longitudinal axis L-L, in opposition to the orientation of the fibers of the fifth layer 209. Additionally, the orientation of the fibers of the fifth layer generally matches the orientation of the fibers of the third layer 205, and generally opposes the orientation of the fibers of the second layer 203. A sixth layer 211 overlays the fifth layer 209 and includes fibers oriented generally at positive forty-five degrees from the longitudinal axis L-L. Thus, orientation of the fibers of the sixth layer 211 generally opposes the orientation of the fibers of the fifth layer 209, and generally matches the orientation of the fibers of the second layer 203. A seventh layer 213 overlays the sixth layer 211 and forms the outer layer of the nail 100. The seventh layer 213 includes fibers oriented generally at ninety degrees to the longitudinal axis L-L. The orientation of the fibers of the seventh layer 213 generally opposes the orientation of the fibers of the fourth layer 207 and generally matches the orientation of the fibers of the first layer 201.

The pattern of the orientations of the layers 201-213 is selected to provide medial portion 100c with physical properties substantially matching the selected physical properties associated with the selected application by including a number of layers with different fiber orientation. Each of the layers contributes to a stiffness in one or more dimension, and the sum of the stiffness provided by each layer approximately equals the selected stiffness in each dimension of interest. In some implementations, and as described above, the pattern of the orientations of the layers 201-213 includes at least two different pairs of layers having generally opposing fiber orientations. The first pair of layers having generally opposing fiber orientations includes the first layer 201 generally across the longitudinal axis L-L, and the fourth layer 207 generally along the longitudinal axis L-L. The second pair of layers having generally opposing fiber orientations includes the second layer 203 at positive forty-five degrees from the longitudinal axis L-L and the third layer 205 at negative forty-five degrees from the longitudinal axis L-L. It should be noted that a third pair of layers having generally opposing fiber orientations includes the fourth layer 207 and the seventh layer 213. However, the generally opposing orientations of the layers of the third pair have the same orientations of the first pair. Similarly, a fourth pair of layers having generally opposing fiber orientations includes the fifth layer 209 and the sixth layer 211, and the opposing orientations of the fourth pair are the same orientations of the second pair.

Additionally, the pattern of the orientations of the layers 201-213 of the nail 100 is symmetric about a middle of the pattern from the first layer 201 to the last layer, i.e. the seventh layer 213. As illustrated, the nail 100 includes seven layers, with the fourth layer 207 being the middle of the layer pattern. Thus, each of the first and seventh layers 201, 213 includes fibers oriented generally across the longitudinal axis L-L, disposed at approximately ninety degrees from the longitudinal axis L-L, each of the second and sixth layers 203, 211 includes fibers oriented generally at positive forty-five degrees from the longitudinal axis L-L, and each of the third and fifth layers 205, 209 includes fibers oriented generally at negative forty-five degrees from the longitudinal axis L-L.

Although the nail 100 has been described as having seven layers 201-213, the nail 100 can include more layers and/or different layer orientation patterns. For example, the number of layers included in the design may be greater or less than seven, and the orientation of the fibers of each layer may be different than as described above. However, the pattern of layer orientations may still include two or more different opposing pairs of fiber orientations and/or the pattern of layer orientations may still be symmetric from a first inner layer to a last outer layer about a middle of the layers or a middle layer. As mentioned above, the specific number of layers and the specific fiber orientation of each layer, together referred to as the design, can be selected to provide the nail 100 with desired performance characteristics during use in a selected application environment.

Figure 4:
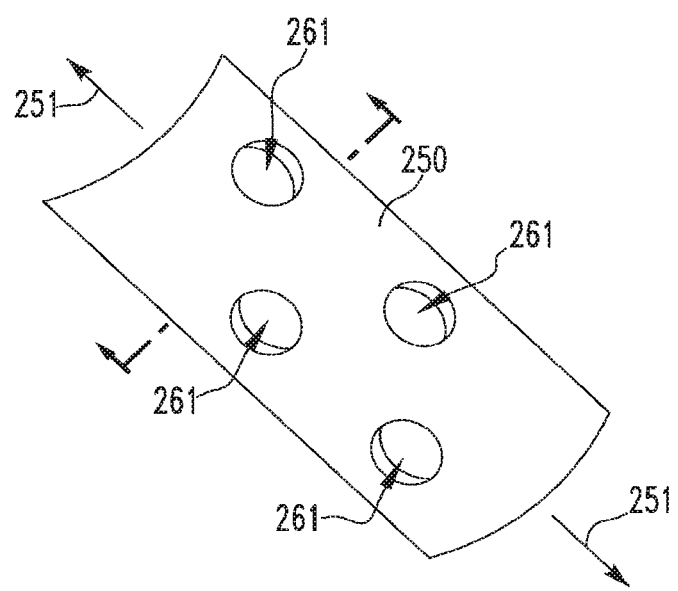
FIG. 4 is a perspective view of an orthopaedic fixation device.
Figure 5:
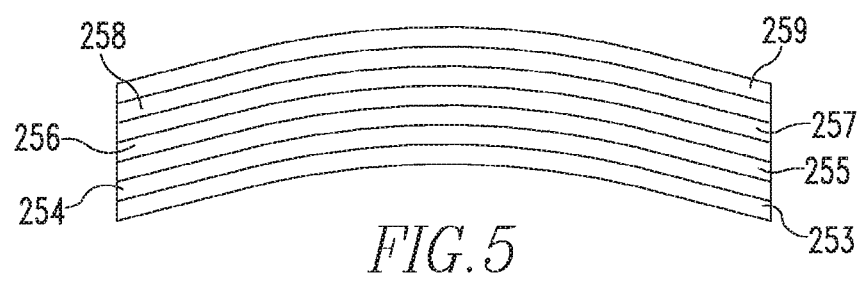
FIG. 5 is a cross-sectional view of the orthopaedic fixation device taken along line 5-5 of FIG. 4.
Figure 6:
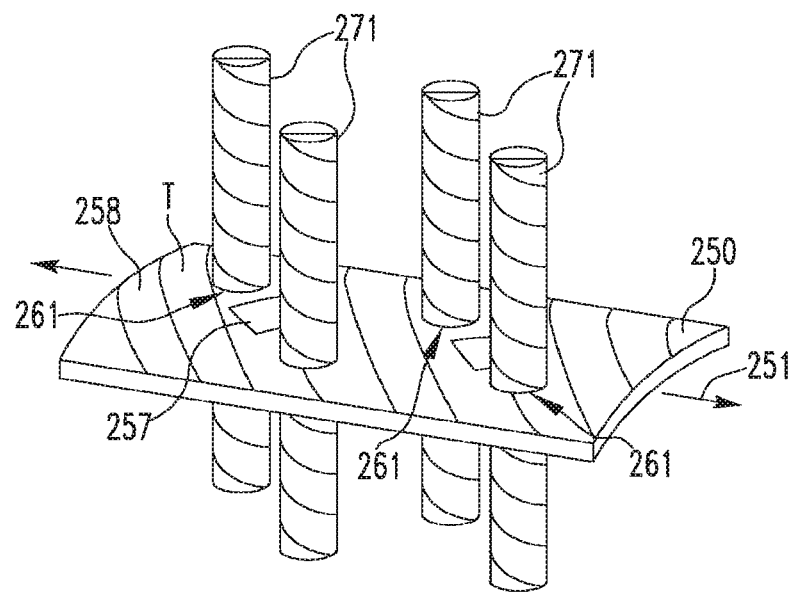
FIG. 6 is a perspective view of an orthopaedic fixation device.

Referring now to FIGS. 4-6 a plate 250 includes a length dimension 251 and has a curvature in a direction across the length dimension 251 to approximately match a curvature of a bone to which the plate 250 is configured to be attached. Apertures 261 are included in the plate 250 and are adapted to receive bone screws, or other fasteners (not shown). The plate 250 includes layers 253-259, which are analogous to layers 203-213 discussed above. However, each of the layers 253-259 can be formed from a sheet of carbon fiber reinforced PEEK material that includes generally parallel continuous carbon fibers. The layers 253-259 are arranged such that the length direction of the carbon fibers is oriented at a selected angle with respect to the length dimension 251 of the plate 250.

Alternatively, as illustrated in FIG. 6, the plate 250 can be formed from a tape, tow, or ribbon by wrapping around guide members 271 located in positions where the apertures 261 are desired. As illustrated, the layer 258 is formed by substantially parallel wraps of a tow at an angle of approximately 45 degrees relative to the length dimension 251. The layer 258 is formed over the layer 257, which is formed by substantially parallel wraps of the tow T at an angle of approximately −45 degrees relative to the length dimension 251. Other layers can include wraps of the tow at approximately 90 degrees to the length dimension 251, at approximately zero degrees to the length dimension 251, or at another selected angle. Additionally, one or more layers of the plate 250 can be formed by weaving the tow T between the guide members 271. Also, one or more layers of the plate 250 can be formed from a sheet, while other layers are formed from a tow. Accordingly, such multi-layer and/or braided carbon fiber/PEEK implants, such as plate 250, are formed such that apertures 261 may be placed in the matrix without causing discontinuity in the fibers, which assists in maintaining implant strength. Another advantage of such multi-layer and/or braided plates is that they exhibit a combination of lower stiffness and relatively smaller dimensions that allow the plates to be more easily implanted in the limited space between bone and muscle as compared to, for example, steel plates.

Figure 7:
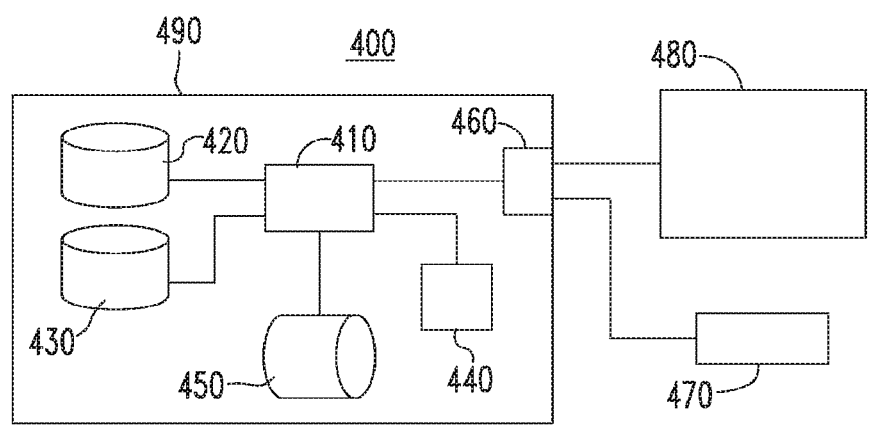
FIG. 7 is a diagram of a system for designing a laminated composite orthopaedic fixation device.

FIG. 7 illustrates a system 400 that can be used to select a design for the nail 100, or other orthopaedic fixation device. The system 400 includes a selection engine 410 operable with a library of models of orthopaedic fixation devices 420, a library of patterns of layer orientations 430, a finite element analysis engine 440, and a storage device 450 for storing instructions for designing a laminate composite orthopaedic fixation device, such as the nail 100. The selection engine 410, the libraries 420 and 430, the finite element analysis engine 440, and the storage device 450 may be formed as components of a computer system 490 that includes a processor, a storage device having an operating system stored thereon, a memory module, and a system bus. The system 400 can further include an input device 470 and an output device 480 operable with an input/output module 460 to receive inputs from a user, such as a selection of performance characteristics, or other description of a desired device for which a design is to be selected, and to provide a selected design to a user. Thus, the selection engine 410 may be formed as a processor of the computer system 490 that executes instructions of a computer program to select a design of a laminated composite orthopaedic fixation device. The library of models 420 and the library of layer orientation patterns 430 may be formed as data structures stored on a storage medium of the computer system 490, such as a magnetic disk or an optical disc. The finite element analysis engine may be formed as the processor of the computer system 490 that executes instructions of a computer program to analyze a design of a laminated composite device.

Each model in the library of models 420 includes internal and external dimension information, such as length, outer circumference, outer diameter, inner diameter, width, and/or shape, or other characteristic of a shell of a device, such as an intramedullary nail or a bone plate. Thus, devices of different configurations, shapes, and sizes may each have an associated model included in the library of models 420. Each model is associated with at least one design in the library of designs 430. The designs associated with a model have a number of layers adapted to fit within the shell of the associated model. For example, a first design associated with a first model of the nail 100 having an outer diameter of 10 millimeters and an inner diameter of 4.4 millimeters over the medial portion 100c may have 20 layers, where each layer is approximately 0.14 millimeters thick. Accordingly, the model includes a hollow central cavity 200a having a diameter of approximately 4.4 millimeters. As discussed above, the nail 100 may have a thermoplastic material, or other material, disposed within the cavity 200a. In some implementations, the model may have an internal diameter of zero, such that the nail 100 is solid, but does not require a cavity to be filled.

A second model may include different external and internal diameters over the medial section than the external and internal dimensions of the first model. The same first design may be associated with the second model where the difference between the internal and external dimension is equal to the difference between the internal and external diameters of the first model, i.e., where the thickness of the medial portion of the second model is the same as the thickness of the medial portion of the first model. Accordingly, each of the designs may be associated with multiple models. Furthermore, where the internal dimension of the orthopaedic fixation device is not critical, the first design may also be associated with nail models where the difference between the internal and external diameters of the nail model is greater than the difference between the internal and external dimensions of the first model. Likewise, the first design may be associated with models of bone plates, or other orthopaedic fixation devices that have a thickness equal to or greater than the thickness of sum of the layers of the design.

Figure 8:
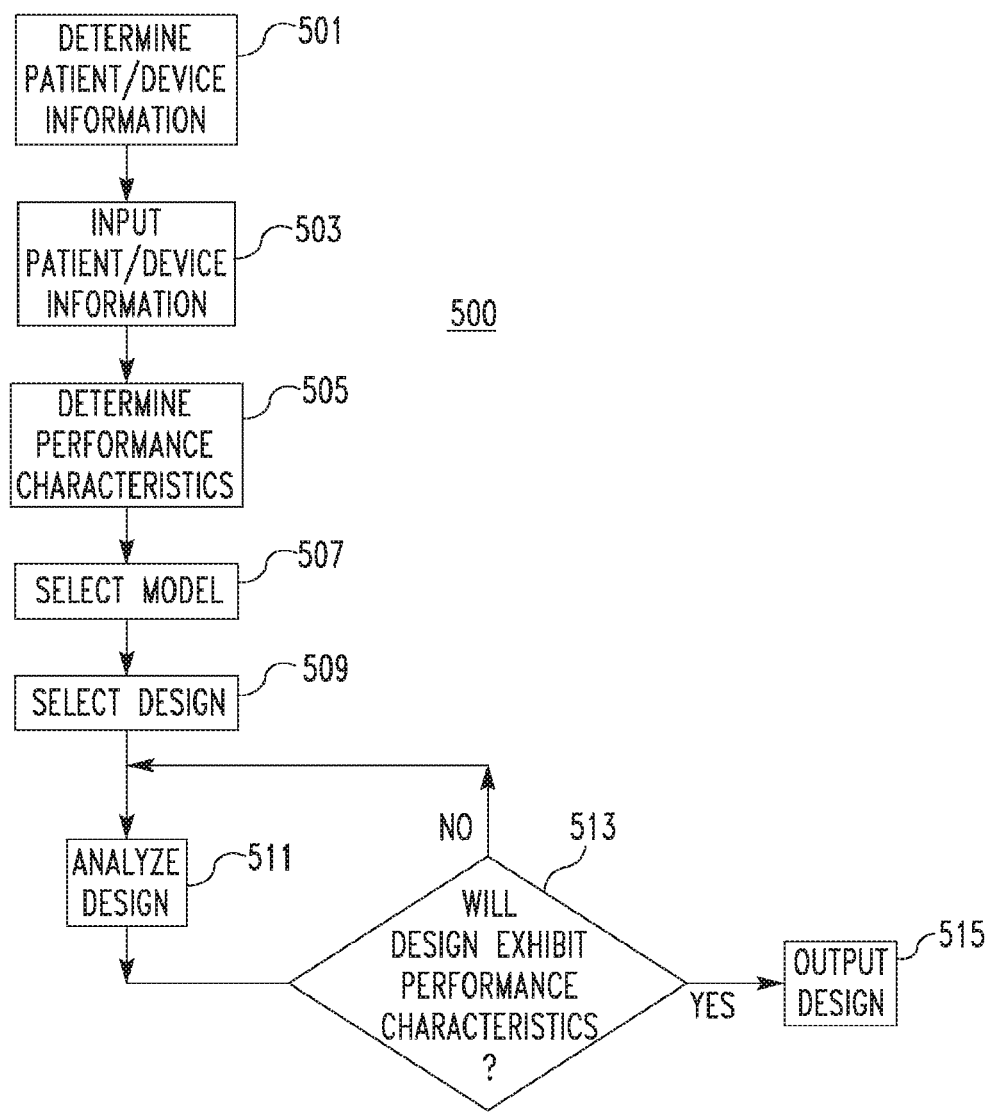
FIG. 8 is flow chart illustrating a process for making a laminated composite orthopaedic fixation device.

As illustrated in FIG. 8, the system 400 can be used to provide a design of a laminated composite orthopaedic fixation device to a user according to a process 500. For example, information pertaining to a patient with whom the device will be used can be determined (501). The information can include, for example, height, weight, age, and health condition of the patient, including a bone mineral density or other measure of bone quality of the patient, a category of device needed, an image, such as a radiograph, of the patient's bone, or other health conditions. The information can be determined by a treating physician, or other healthcare provider, and can be input (503) to the system 400 for use in providing a design of a laminated composite fixation device. The information can be input by the physician or other healthcare provider at the treatment facility using a terminal operable with the system 400. For example, the input device 470 may be a remote terminal operable with the computer 490 over a network, such as the Internet. Alternatively, the information may be sent to an operator of the system 490 at a manufacturer or supplier of the laminated composite fixation device.

Additionally, device information may be determined (501) by the physician or other healthcare provider and input (503) to the system 400. For example, the physician may determine a configuration of the device that is appropriate for use in a prescribed treatment for the patient, such as an antegrade femoral nail. Additionally, a length or other external dimension of the device may be determined by the physician based on the patient information, such as a radiograph of the patient's bone to which the device is to be attached. The device information can include fixed external dimension, such as a diameter, for each section of the device, such as a diameter of the first section 101, a diameter of the medial portion 100c, and a diameter of the second section 103. The device information can additionally include a minimum internal diameter to ensure that a cavity of a minimum diameter is included in the device. As discussed above, this minimum diameter can be zero, if desired. Where a minimum internal diameter is included, a design having fewer than the maximum number of layers may be selected, as discussed in greater detail below, thereby providing a larger internal diameter than the minimum internal diameter. Alternatively, the device information can include a fixed internal diameter such that a thickness of the device and a size of any hollow cavity can be set.

Performance characteristics of the laminated composite device are also determined (505). The performance characteristics may be determined by the physician or other healthcare provider, based on the patient information and performance characteristics can then be input to the system 400. For example, a compression stiffness, a bending stiffness, and/or a twisting stiffness of the laminate composite device may be determined by the physician based on the patient's weight and the age of the patient. Alternatively, a maximum compression deflection, a maximum bending deflection, and/or a maximum torsion deflection can be determined by the physician, and the system 400 can automatically determine the stiffness based on the patient information, the device information, and/or default information. The age may be used to adjust the performance characteristics of the composite device, such as by increasing the compression stiffness, the bending stiffness, and/or the twisting stiffness for a younger patient, who may be more active than an older patient. Additionally, a compression stiffness of the laminated composite device may be reduced based on an age of the patient to account for a reduced stiffness of the patient's bone, such that shielding of the bone by the laminated composite device may be reduced or eliminated. Similar adjustments can be made based on the bone mineral density, or other patient information, including imaging information.

In another example, the performance characteristics of the laminated composite device may be determined based on an indication of an isotropic device, such as a metal device that may otherwise have been prescribed for the patient. The system 400 may determine that the dimensions of the laminated composite device are substantially the same dimensions as those of the isotropic device. The system 400 may further determine the compression stiffness, the bending stiffness, and/or the twisting stiffness of the laminate composite device based on the compression stiffness, the bending stiffness, and/or the stiffness strength of the isotropic device. The determination of the performance characteristics based on the isotropic device may include adjustment of the performance characteristics of the isotropic device based on such factors as the age of the patient, a bone mineral density of the patient, or other factor that may be considered by a physician in selecting the performance characteristics, as described above.

For example, an isotropic titanium device can be identified for use in selection of the performance characteristics of the laminated composite device. In such an example, a length, inner diameters, outer diameters, bends, and/or other dimension and shape information for the laminated composite device can be determined by reference to the analogous information for the selected isotropic titanium device. The compression stiffness, the bending stiffness, and/or the twisting stiffness of the laminate composite device can be determined by automatically adjusting the corresponding stiffness values of the isotropic titanium device. Particularly, one or more the stiffness values of the isotropic titanium device may be reduced to derive the corresponding stiffness values of the laminated composite device.

Reducing the stiffness values can lower the occurrence of undesirable bone mineral density loss in the bone to which the device is attached, which has been observed in some applications employing metallic fixation devices. Particularly, such bone mineral density reductions are believed to occur due to a "shielding" of the bone from loads due to a relatively higher stiffness of the implant compared to healthy bone. The implant, which can remain implanted in the patient for extended periods, is believed to bear a disproportionately large portion of forces under normal circumstances, and, as a result, it is believed that the body resorbs bone minerals. While this action is believed to be accurate, it is not intended to necessarily form part of the claimed subject matter, except where specifically recited in the claims.

The system 400 then selects a model from the library of models 420 according to the input device information and/or patient information (507). The model includes internal and external dimensions of the laminate composite device that limit the size and shape of the laminate composite device. Accordingly, the model can be selected such that the external dimensions of the laminate composite device do not exceed the dimensions selected based on the patient information. The model can also be selected to have the minimum (or fixed) internal dimension, such that a model having the most designs associated therewith is selected, whereby chance of selecting of a design meeting the input performance characteristics, as discussed below, is increased.

The system 400 then selects a first design (509) from the library of designs 430 that is associated with the selected model. For example, the system may select a first design from among the designs associated with the selected model having a fewest number of layers, a lowest manufacturing cost, or based on other criteria, or no criteria (i.e., random or pseudo-random selection). The system 400 then performs a finite element analysis on the selected design (511) and determines whether the results of the finite element analysis indicate that the selected design will exhibit the selected performance characteristics (513). If the system 400 determines that the selected design will exhibit the selected performance characteristics, then the selected design is output (515). The selected design can be output in tangible or electronic form, such as in the form of instructions operable to cause an automated manufacturing system to manufacture the laminate composite device according to the design.

The selected design may additionally include information about a shape of the device, which may be determined and input by a physician or other healthcare provider, or which may be determined by the system 400 based on the input patient information, such as an image of the patient's bone. If output in the form of instructions, the design can include instructions operable to automatically create a device having the shape of the design. Alternatively, the device can be shaped after manufacture, either manually or automatically, such as by thermoforming. For example, the desired shape may be obtained by heating or otherwise exciting the device until the plastic material is malleable, bending the device to the desired shape, and allowing the plastic material to set. Additionally, or alternatively, the shape of the device may be adjusted intraoperatively, such as during implantation of the device. Accordingly, some or all of the designs in the library of designs 430 can be for straight devices, or devices having a default shape, based on the configuration of the device.

If the system 400 determines that the selected design will not exhibit the selected performance characteristics, then the system 400 selects a second design from among the designs associated with the selected model (509). The system 400 then analyzes the second design (511) and determines whether second design will exhibit the selected performance characteristics. The selection (509), analysis (511) and determination (513) are repeated until it is determined that a selected design will exhibit the selected performance characteristics. Additionally, the process 500 can include a determination that no more designs are available for selection. Thus, where a fixed internal dimension is provided, or a fixed thickness is provided, and relatively few designs will fit between the fixed external dimension and the fixed internal dimension, or will provide the fixed thickness, the system may not loop continuously in selecting designs when none of the relatively few designs will exhibit the selected performance characteristics. The system 400 can instead select the design having performance characteristics that most closely match the selected performance characteristics, or the system 400 can output an indication that no designs match the selected performance characteristics.

Figure 9:
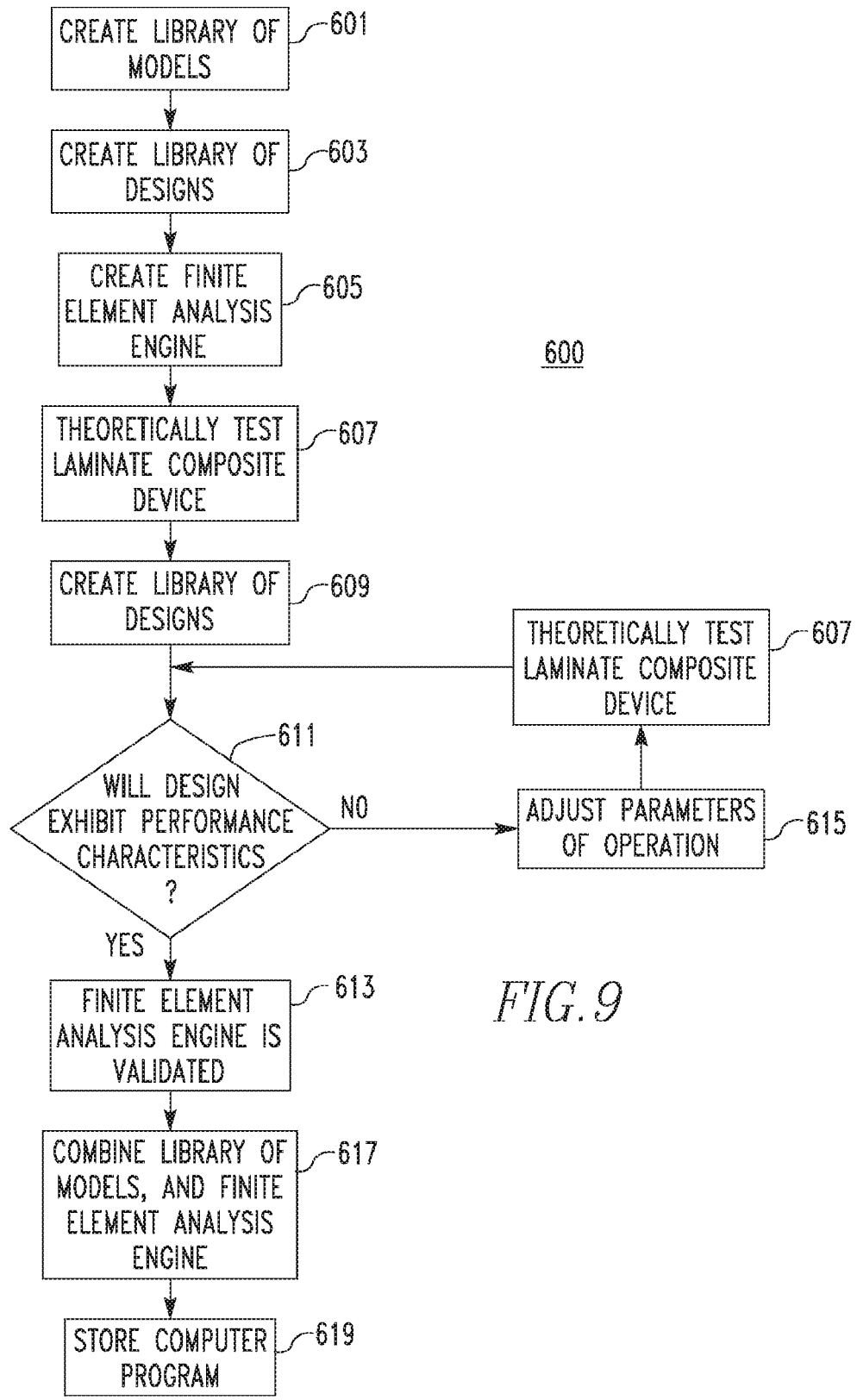
FIG. 9 is a flow chart illustrating a process for making the system of FIG. 7.

Referring now to FIG. 9, a flow chart illustrates a process 600 for making the system 400. According to the process 600, the library of models 420 may be created (601) by determining and storing internal and external dimensions and a configuration for each of multiple isotropic devices, such as metal orthopaedic fixation devices. Performance characteristics of the isotropic devices may also be determined and stored in association with a corresponding model. Alternatively, or additionally, some or all of the models may not correspond to isotropic devices. Different models may also be included for fixed dimension inputs and for minimum (or maximum) dimension inputs. Thus, one model for use with minimum internal diameter intramedullary nail inputs may have a first group of designs associated therewith, while another model having the same external dimension but for use with a fixed internal diameter may have a second group of designs associated therewith. Where the models are for fixed and minimum internal dimensions of an intramedullary nail, and each has a fixed external dimension, the second group is a subset of the first group, with the first group including additional designs that will produce a larger internal cavity (even where the cavity is subsequently filled).

The library of designs 430 may be created (603) by storing symmetric patterns of layer orientations that include two or more opposing pairs of layer orientations. Each design of the library of designs 430 may be associated with one or more model of the library of models 420 based on whether the number of layers of a design will fit within the shell of a model. Additionally, designs of greater thickness and/or more layers can be stored as a symmetric repetition of other symmetric patterns. The designs can also be stored as a symmetric repetition of another symmetric pattern with the inclusion of an extra layer in the center. A number of exemplary designs are included in table 1, in which "th" represents an angle from 0 degrees to 90 degrees, a numeral following a bracketed pattern of layer angles denotes that the pattern is repeated a number of times equal to the numeral, and the letter "S" denotes that the bracketed pattern, repeated a number of times equal to the numeral if one is present, is repeated in reverse. Additionally, the "†" symbol denotes that a 90 degree layer has been added between the pattern and its reverse repetition, and the symbol "‡" denotes that a 5 degree layer has been added between the pattern and its reverse repetition.

TABLE 1

| Design | Number of Design layers |
| --- | --- |
| [5/th/-th/90/-th/th/5] | 7 |
| [90/th/-th/5/-th/th/90] | 7 |
| [5/th/-th/90/90/-th/th/5] | 8 |
| [90/th/-th/5/5/-th/th/90] | 8 |
| [5/5/th/-th/90/-th/th/5/5] | 9 |
| [5/5/th/-th/90/90/-th/th/5/5] | 10 |
| [90/90/th/-th/5/5/-th/th/90/90] | 10 |
| [5/5/th/-th/90/90/90/-th/th/5/5] | 11 |
| [90/90/th/-th/5/5/5/-th/th/90/90] | 11 |
| [5/th/th/-th/-th/90/-th/-th/th/th/5] | 11 |
| [5/5/5/th/-th/90/90/-th/th/5/5/5] | 12 |
| [5/th/th/-th/-th/90/90/-th/-th/th/th/5] | 12 |
| [90/th/th/-th/-th/5/5/-th/-th/th/th/90] | 12 |
| [5/5/5/th/-th/90/90/90/-th/th/5/5/5] | 13 |
| [5/th/th/-th/-th/90/90/90/-th/-th/th/th/5] | 13 |
| [90/th/th/-th/-th/5/5/5/-th/-th/th/th/90] | 13 |
| [5/th/-th/90/-th/th/5]S | 14 |
| [5/th/-th/90/-th/th/5/5/th/-th/90/-th/th/5] | 15 |
| [5/th/-th/90/-th/th/5/90/5/th/-th/90/-th/th/5] | 15 |

TABLE 1-continued

| Design | Number of Design layers |
|---|---|
| [5/th/-th/90]2S | 16 |
| [5/5/5/th/th/-th/-th/90/90/-th/-th/th/th/5/5/5] | 16 |
| [5/5/th/th/-th/-th/90/90/90/90/-th/-th/th/th/5/5] | 16 |
| [90/90/th/th/-th/-th/5/5/5/5/-th/-th/th/th/90/90] | 16 |
| [5/5/5/th/th/-th/-th/90/90/90/-th/-th/th/th/5/5/5] | 17 |
| [5/5/th/th/-th/-th/90/90/90/90/90/-th/-th/th/th/5/5] | 17 |
| [5/5/th/th/-th/-th/90/90/5/90/90/-th/-th/th/th/5/5] | 17 |
| [90/90/th/th/-th/-th/5/5/5/5/5/-th/-th/th/th/90/90] | 17 |
| [90/90/th/th/th/th/5/5/90/5/5/th/th/th/th/90/90] | 17 |
| [5/5/th/-th/90/-th/th/5/5]S | 18 |
| [5/5/5/th/th/-th/-th/90/90/90/90/-th/-th/th/th/5/5/5] | 18 |
| [5/5/th/th/-th/-th/90/90/5/5/90/90/-th/-th/th/th/5/5] | 18 |
| [5/5/th/-th/90/-th/th/5/5/90/5/5/th/-th/90/-th/th/th/5/5] | 19 |
| [5/th/th/-th/-th/90/90/-th/th/5/5/th/-th/90/90/-th/-th/th/th/5] | 20 |
| [5/5/th/-th/90/90/-th/th/5/5/90/5/5/th/-th/90/90/-th/th/5/5] | 21 |
| [5/5/th/-th/90/90/90/-th/th/5/5]S | 22 |
| [5/5/th/-th/90/90/90/-th/th/5/5]S† | 23 |
| [90/90/th/th/5/5/5/th/th/90/90]S‡ | 23 |
| [5/th/th/-th/-th/90/90/-th/-th/th/th/5]S | 24 |
| [90/th/th/-th/-th/5/5/-th/-th/th/th/90]S | 24 |
| [5/th/-th/90/90/-th/th/5]3 | 24 |
| [90/th/-th/5/5/-th/th/90]3 | 24 |
| [5/5/5/th/-th/90/90/-th/-th/th/5/5/5]S† | 25 |
| [5/th/th/-th/-th/90/90/-th/-th/th/th/5]S† | 25 |
| [90/th/th/-th/-th/5/5/-th/-th/th/th/90]S‡ | 25 |
| [5/th/th/-th/-th/90/90/90/-th/-th/th/th/5]S | 26 |
| [90/th/th/-th/-th/5/5/5/-th/-th/th/th/90]S | 26 |
| [5/th/th/-th/-th/90/90/90/-th/-th/th/th/5]S† | 27 |
| [90/th/th/-th/-th/5/5/5/-th/-th/th/th/90]S‡ | 27 |
| [5/th/-th/90/-th/th/5]2S | 28 |
| [5/th/-th/90/-th/th/5]2S† | 29 |
| [5/th/-th/90/-th/th/5/5/5/th/-th/90/-th/th/5]S | 30 |
| [5/th/-th/90/-th/th/5/90/5/th/-th/90/-th/th/5]S | 30 |

Alternatively or additionally, non-symmetric patterns and/or patterns with less than two (including zero) opposing pairs or layer orientations can be stored.

The finite element analysis engine 440 may be created (605) by selecting one or more parameters for operation of a finite element analysis program. A laminate composite device of a first design is then theoretically tested using the finite element analysis program and the selected parameter(s) for operation (607) to generate theoretical test results. Additionally, the laminate composite device of the first design is physically tested (609) to generate physical test results. The theoretical and physical test results are compared (611) to determine whether the theoretical test results are similar to the physical test results. If the theoretical and physical test results are similar, then the finite analysis engine is validated (613). If the theoretical and physical test results differ substantially, then the parameters for operation are adjusted (615), and the theoretical testing of the laminate composite device of the first design is repeated (607) to generate new theoretical test results, which are then compared (611) to the physical test results.

The library of models 420, the library of designs 430, and the validated finite element analysis engine 440 may be combined (617) with a computer system having a processor 410, a storage device 450, and an input/output module 460. A computer program is stored (619) on the storage device 450 such that the computer program is operable with the processor 410. The computer program can include instructions that, when executed by the processor 410, are operable to cause performance of the process 500 for providing a design for a laminated composite device.

Described below are implants made from a carbon fiber-reinforced composite material or a fiber-reinforced biocompatible polymer, such as polyetheretherketone (PEEK) or polyaryletherketone (PAEK). The implant may be a nail, plate, hip stem, shoulder stem, spine cage or other implantable device for orthopaedic application. The features described in conjunction with some of the embodiments have been illustrated as an antegrade femoral nail or a bone plate, but these features may be equally applied in at least a humeral, tibial, radial, ulnar, clavicular, and fibular application. Further, while the features described in conjunction with some of the embodiments have been illustrated as trauma applications, they could equally be applied to reconstructive products.

Figure 10:
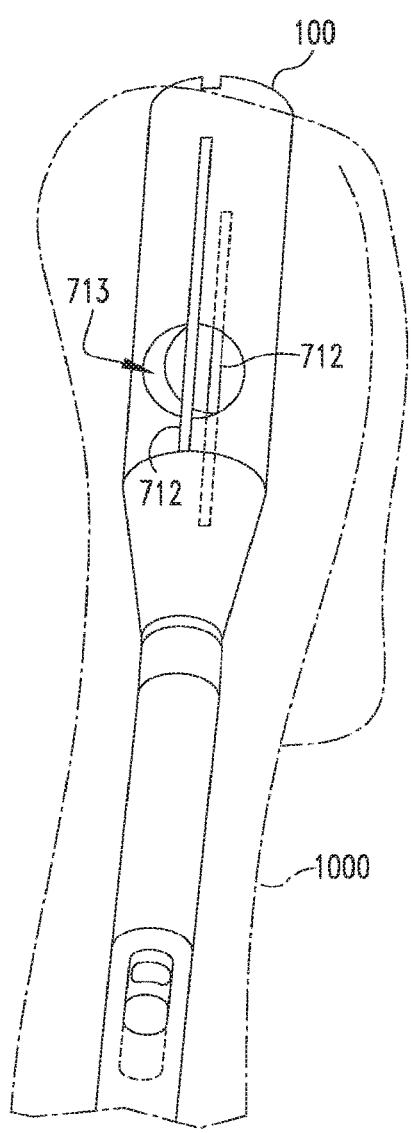
FIGS. 10 and 11 illustrate an intramedullary nail in a medial-lateral view in a first embodiment.
Figure 11:
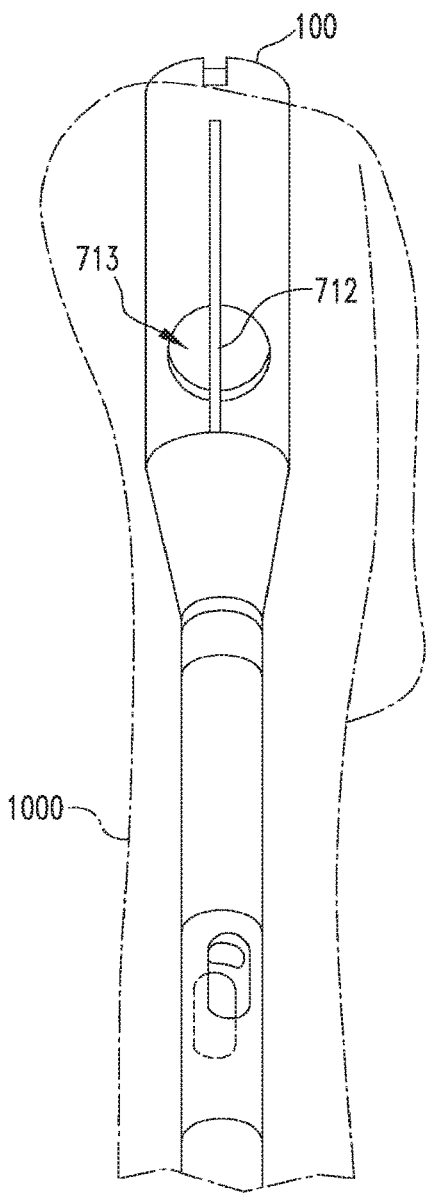

FIGS. 10 and 11 illustrate an intramedullary nail 100 mounted within a bone 1000. The intramedullary nail may have one or more features as described above. In the depicted embodiments, the intramedullary nail 100 is made from a carbon fiber-reinforced composite material or a fiber-reinforced biocompatible polymer. As an example, the material may be the ENDOLIGN product available from Invibio Inc., located at 300 Conshohocken State Road, West Conshohocken, Pa. ENDOLIGN is a registered trademark of Invibio Limited. As another example, the material may be a high strength version of polyetheretherketone, commonly known as PEEK. In some embodiments, the intramedullary nail 100 includes a hole 713, which may be used to receive a lag screw (not shown). In some embodiments, the intramedullary nail 100 may be cannulated.

In FIGS. 10 and 11, the intramedullary nail 100 includes radio-opaque markers 712. The radio-opaque markers 712 may be imbedded metal wire placed at various locations on or in the intramedullary nail 100. One set of markers may be placed along the axis of the intramedullary nail 100 on the medial and lateral side. These markers are used with an imaging device in a medial/lateral view to determine the proper rotation of the intramedullary nail 100 to ensure that the lag screw is placed into the center of the bone 1000. It is accomplished by aligning the two markers 712 with a center of the bone 1000 as is shown in FIG. 11.

The radio-opaque markers 712 may be made from a variety of materials, including but not limited metals (such as 316 SST, Cobalt Chrome, Ti 6Al 4 V, tantalum), ceramics (such as TCP, HA, Barium Sulfate), resorbable materials such as magnesium, or polymers. The radio-opaque markers 712 can take the shape of a single element or multiple elements. The radio-opaque markers 712 may be continuous or non-continuous. The radio-opaque markers 712 may mark the axis of a screw path with individual markers on each side of the intramedullary nail 100, or have multiple markers on each side that note the edges of the screw path.

In some embodiments, a fastener may be used in conjunction with the nail. As examples, the fastener may be a locking screw, a lag screw, or a compression screw. The fastener may be made from metal, polymer, or a composite material. The fastener may include a radio opaque marker to help with alignment or depth insertion. The fastener may be threaded and may include a radio opaque marker only on the thread portion to provide an indication of bone purchase.

Figure 13:
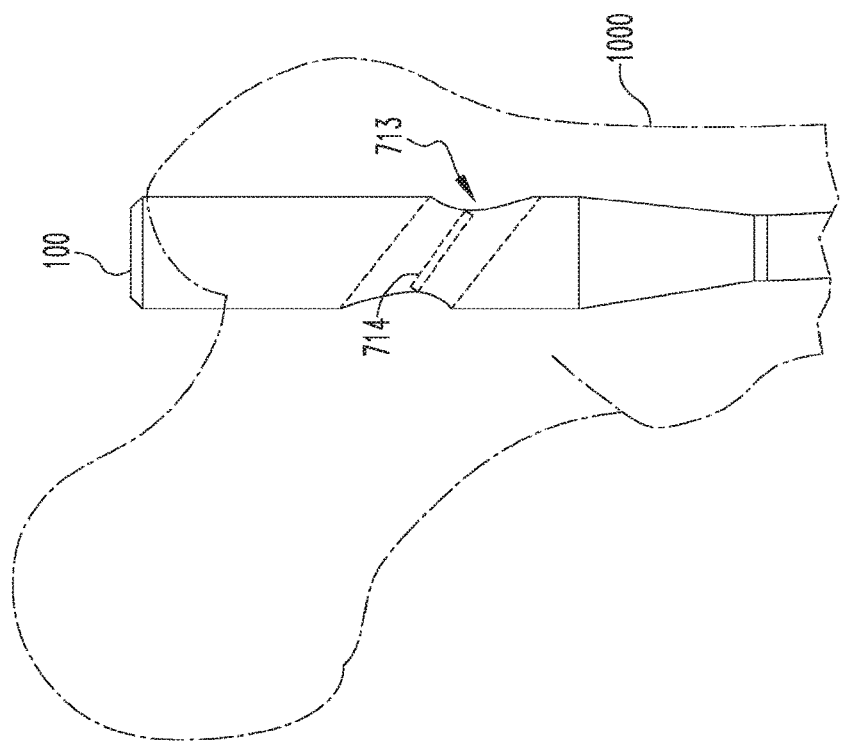
FIGS. 12 and 13 illustrate an intramedullary nail in an anterior-posterior view in a second embodiment.
Figure 12:
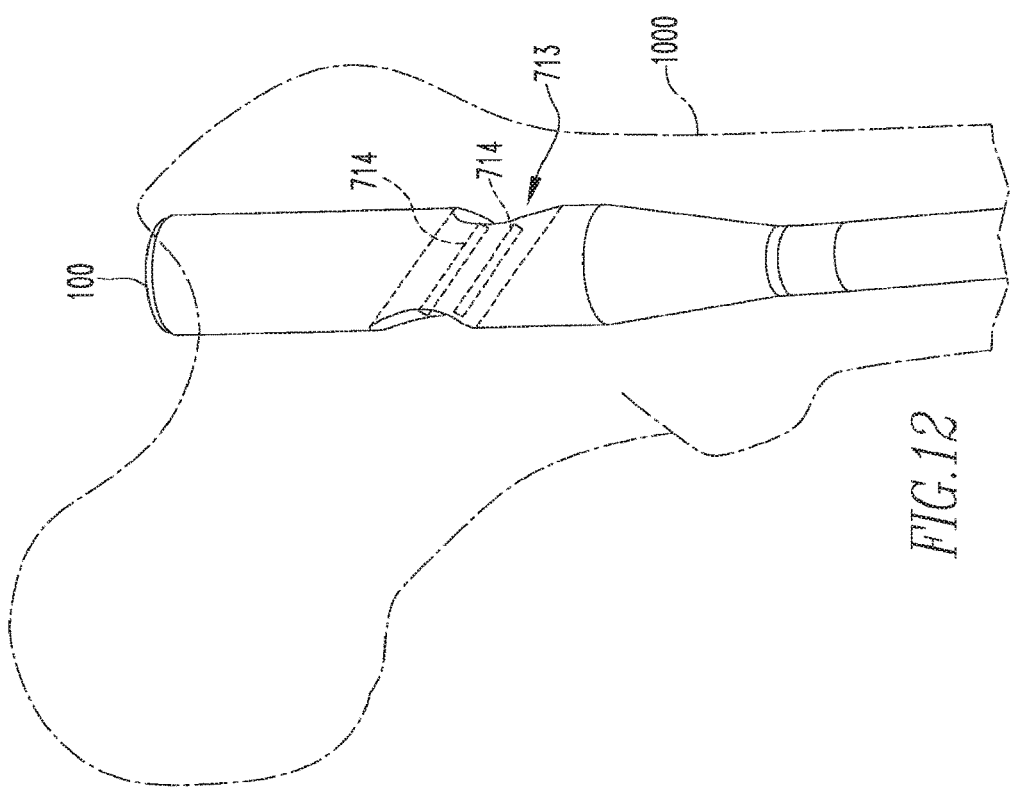
Figure 14:
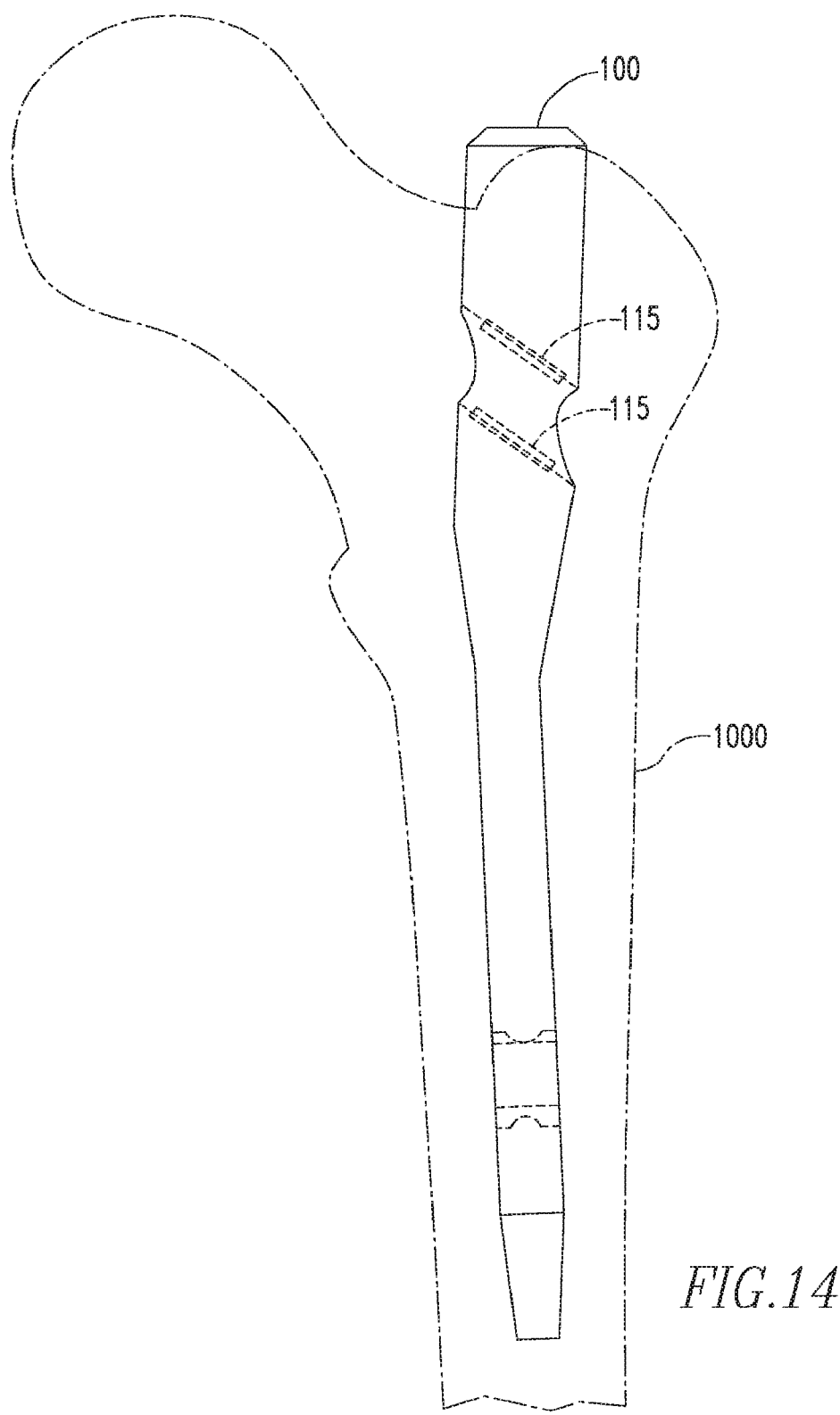
FIGS. 14-17 illustrate an intramedullary nail in a third embodiment.

FIGS. 12 and 13 illustrate another use of the radio-opaque markers. In the depicted embodiment, one set of radio-opaque markers 714 is placed on the anterior and posterior side of the intramedullary nail 100 in the same plane as the axis of the lag screw hole 713. These markers are used in conjunction with an imaging device in an anterior/posterior view to determine the correct depth of the nail by aligning the markers with the bone 1000.

Figure 15:
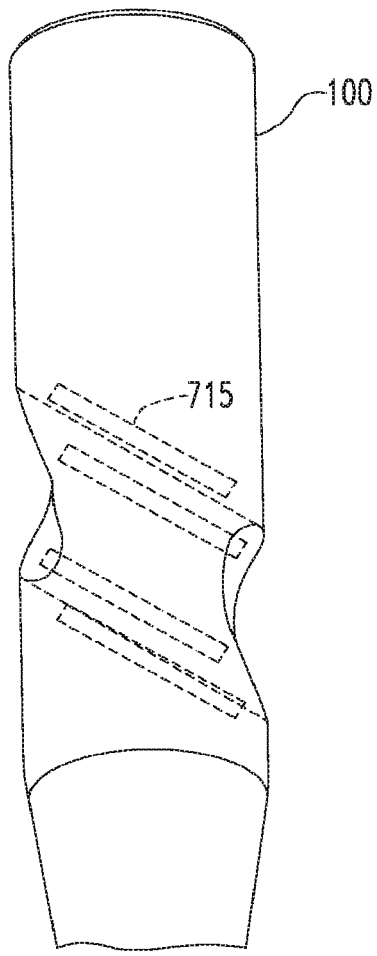
Figure 16:
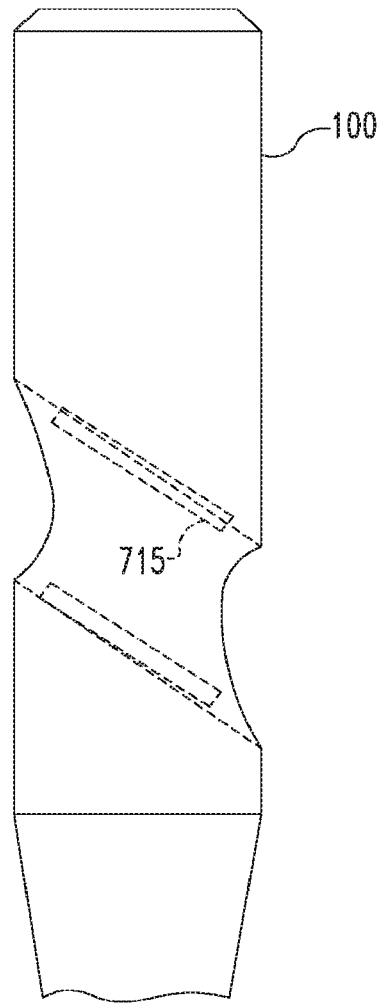
Figure 17:
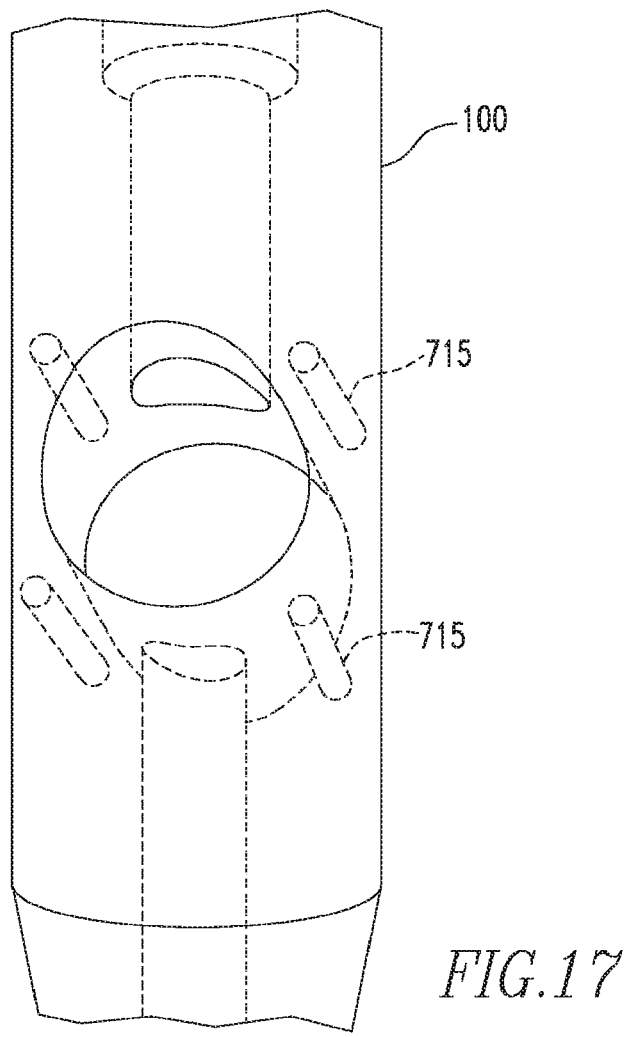

FIGS. 14-17 illustrate an alternative placement of radio-opaque markers. In the depicted embodiments, the radio-opaque markers 715 are placed on each side of the screw path. In FIG. 15 the imaging device is misaligned with the markers and aligned in FIG. 16. FIG. 17 illustrates a perspective view of the placement of four markers 715. In the embodiment depicted in FIG. 17, four markers are shown but those of ordinary skill in the art would understand that two or more markers may be used. Further, it should be noted in the embodiment depicted in FIG. 17 that the markers are not placed in the thinnest area next to the hole. This may be significant for the structural integrity of the implant.

Figure 18:
FIG. 18 illustrates a sectional side view of an intramedullary nail in a fourth embodiment.

FIG. 18 illustrates another embodiment of the intramedullary nail 100. In the depicted embodiment, the intramedullary nail 100 includes a core 716 surrounded by a polymer or composite material. The core 716 may be made from any biocompatible material, such as a metal, ceramic, polymer, or a composite. In the depicted embodiment, the core 716 has a cylindrical cross-section but other geometries may be equally used. The core 716 may be placed over the mandrel during manufacture of the nail or used in place of a mandrel.

Figure 19:
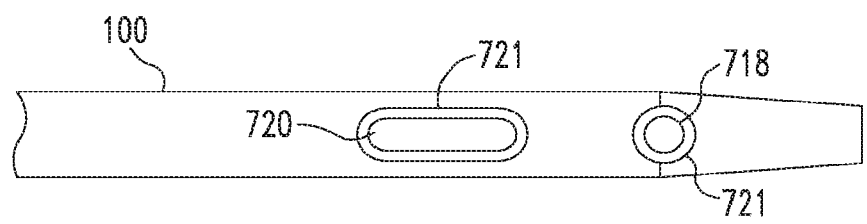
FIG. 19 illustrates a sectional side view of an intramedullary nail in a fifth embodiment.

FIG. 19 illustrates another embodiment of the intramedullary nail 100. The intramedullary nail 100 may include one or more openings at a distal end. In the depicted embodiment, the intramedullary nail 100 includes a hole 718 and a slot 720, and each opening includes an insert 721. The insert 721 may be integral or embedded into the intramedullary nail 100. The insert 721 may be made from any biocompatible material, such as a metal ceramic, polymer, or a composite. The insert 721 may be radio-opaque such that a more distinct image in the radiograph making the technique of acquiring "perfect circles" easier. In some embodiments, the insert 721 may include a flange. For example, the flange may conform to the exterior surface of the nail. The insert 721 may provide additional strength and abrasion resistance. For example, the insert 721 may prevent an instrument, such as a drill, from wearing of the composite material. Those having ordinary skill in the art would understand that the location of the hole 718 and the slot 720 may be reversed. Further, additional holes or slots may be provided, and in some embodiments one of the hole or slot may be omitted.

Figure 20:
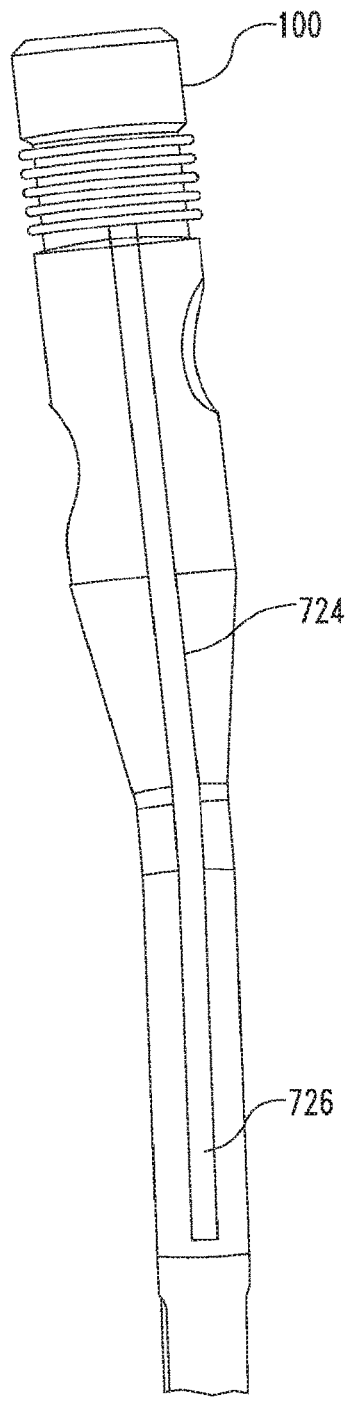
FIG. 20 illustrates an intramedullary nail in an anterior-posterior view in a sixth embodiment.
Figure 21:
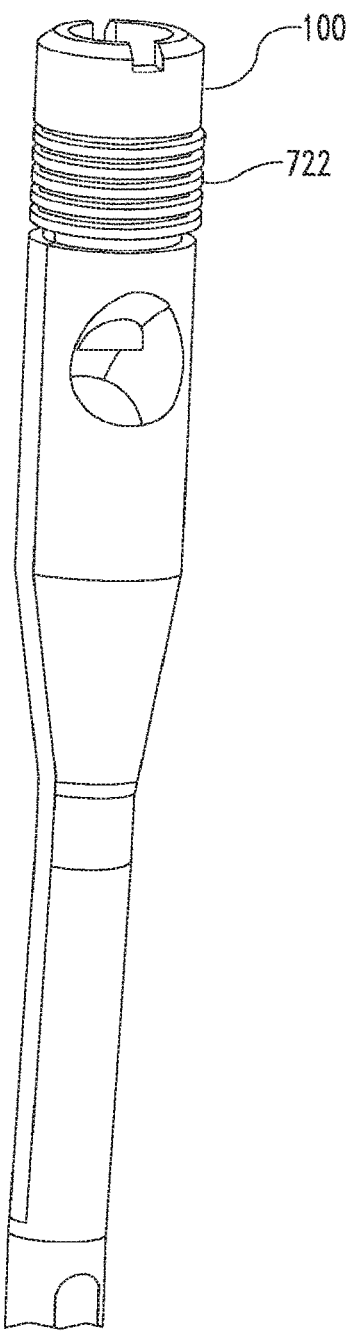
FIG. 21 illustrates the intramedullary nail shown in FIG. 20 in a medial-lateral view.
Figure 27:
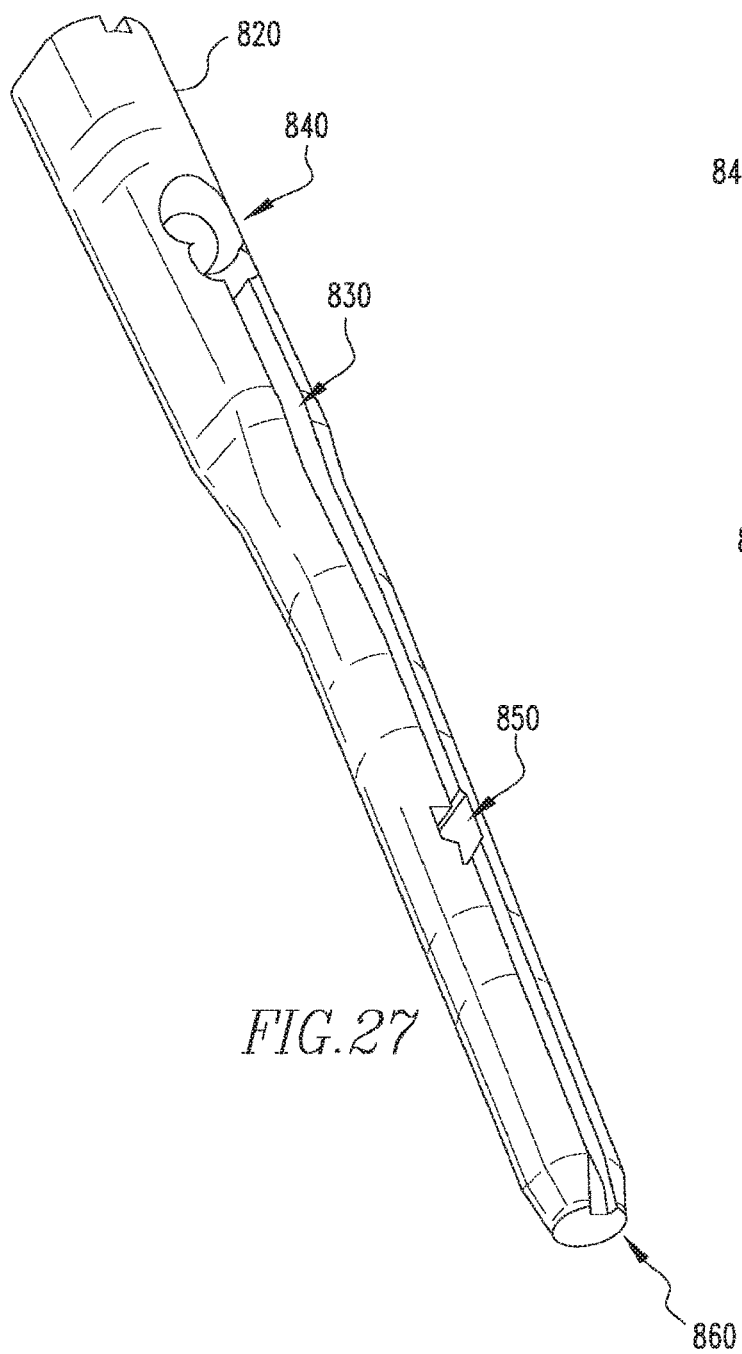
Figure 28:
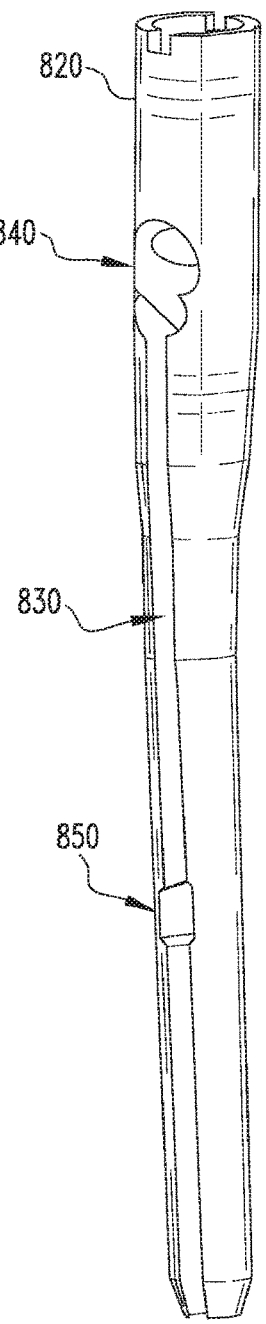

FIGS. 20 and 21 illustrate another embodiment of the intramedullary nail 100. The intramedullary nail may have one or more features as described above. In the depicted embodiment, the intramedullary nail 100 includes embedded or in-molded electronic components. As examples, the electronic components may include one or more of a transceiver 722, wire 724, and strain gauge/circuit board 726. As yet another example, the intramedullary nail 100 may include a thin-film battery (not shown), such as the device disclosed in U.S. Pat. No. 6,632,563 to Krasnov et al. or U.S. Pat. No. 4,960,655 to Hope et al. The '563 patent and the '655 patent are herein incorporate by reference. The thin-film battery may form part of an energy scavenging and storage device. Scattered ambient energy present in the form of ubiquitous vibrations, such as heat or radiation, can be harvested from a variety sources by utilizing piezoelectric, thermoelectric, or photovoltaic generators. The harvested energy can then be stored in the thin-film battery. Embedding electronic components within the orthopaedic fixation device provides the advantages of increased biocompatibility and reduced interference from electromagnetic forces.

As an example, the energy scavenging device may be one or more thin-film, all-solid-state, lithium energy cells provided by Front Edge Technologies of Baldwin Park, Calif. The energy cell may be placed between two layers of carbon fiber. As an example, the layers may be at 90 degrees to each other. The energy cell may be located squarely in the geometric center of the two layers. A polyester-coated flat flexible cable (FFC) may be used to connect the energy cell to other components. As an example, the flat flexible cable may be obtained from Nicomatic Inc. of Warminster, Pa. The energy cells may be pre-sealed along the edges and over the electrodes with a two component low-viscosity epoxy and cured at room temperature. As an example, the epoxy may be Epotech, #301. The curing time may be from 18-30 hours, and more particularly 24 hours.

In some embodiments, the intramedullary nail 100 may be patient specific. The intramedullary nail may have one or more features as described above. As best seen in FIG. 22, portion 728 may be removed to achieve a custom length, hole 730 may be added, hole 732 may be changed from a static hole to a dynamic hole, and a radius R may be changed to achieve to match a patient's bone. These patient-specific modifications may be performed pre-operatively or intraoperatively. A polymer material presents the advantage of 5 intraoperatively adjusting the orthopaedic fixation device. In the past, bending a metal nail required a machine strong enough to bow the nail. Such a machine is generally considered to be too cost prohibitive for placement in an operating room. For a polymer device, other forms of energy may be used to reshape the intramedullary nail. As examples, such energy may be in the form of heat or acoustic energy, such as ultrasound. As an example, energy may be o applied to the intramedullary nail and then manually shaped. Alternatively, the intramedullary nail may be placed in a three-roll bender with the energy directed between the rollers for intraoperatively shaping the intramedullary nail. Similarly, additional holes or other features may be obtained by applying energy in conjunction with a specific geometric fixture to control shape and location. 5

FIG. 23 illustrates another embodiment of the intramedullary nail 100. The intramedullary nail may have one or more features as described above. In the depicted embodiment, a protective sleeve or capsule 734 may be embedded within the intramedullary nail 100. The protective sleeve 734 may be made of a ceramic material or a metal with a heat resistant coating. The material may be selected to reduce the chance of electromagnetic0 interference. The protective sleeve 734 may be used to protect an electronic component, such as a sensor. The protective sleeve 734 may be used to provide a hermetic seal. The protective sleeve 734 may be placed at any radial depth of the intramedullary nail 100.

FIG. 24 illustrates still another embodiment of the intramedullary nail 100. The intramedullary nail may have one or more features as described above. In the5 depicted embodiment, the intramedullary nail 100 includes an in-molded cannulation 736 and one or more in-molded holes 738. In other words, the cannulation or the hole is manufactured contemporaneously with the intramedullary nail and is not a result of a later manufacturing step. A mandrel or similar device may be used to create such voids. FIG. 24 also illustrates the embedded sleeve or capsule 734.

FIGS. 25 and 26 illustrate yet another embodiment of the intramedullary nail 810. In the depicted embodiment, the intramedullary nail 810 has a generally "U" or "C" shaped cross-section. The depicted embodiment is easier to manufacture than a cannulated intramedullary nail but still allows for the use of a guide rod. The intramedullary nail 810 may be manufactured by assembling layers of a composite and then shaping or by shaping in manufacture, such as by molding.

FIGS. 27-30 illustrate an intramedullary nail 820 with a groove or channel 830. The depicted embodiments are easier to manufacture than a cannulated intramedullary nail but still allows for the use of a guide rod. The intramedullary nail 820 may also include a proximal hole 840, a distal hole 850, and a tapered tip 860. In the embodiment depicted in FIG. 29, the proximal hole 840 is generally cylindrical and the distal hole 850 is slotted but other shapes may equally be used. In the embodiment depicted in FIG. 30, the intramedullary nail 820 has a trapezoidal shape but other shapes may also be used.

In operation, a guide rod is placed into an intramedullary canal. The fracture is reduced. The intramedullary nail 820 is placed in the intramedullary canal with the guide rod riding in the channel 830. The guide rod is removed, and the intramedullary nail 820 is locked into place.

Figure 31:
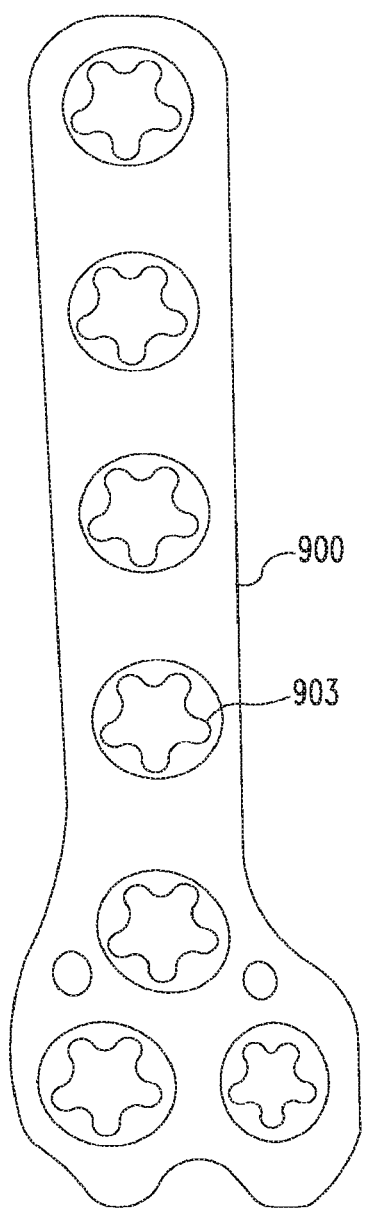
FIGS. 31 and 32 illustrate bone plates in a first embodiment.
Figure 32:
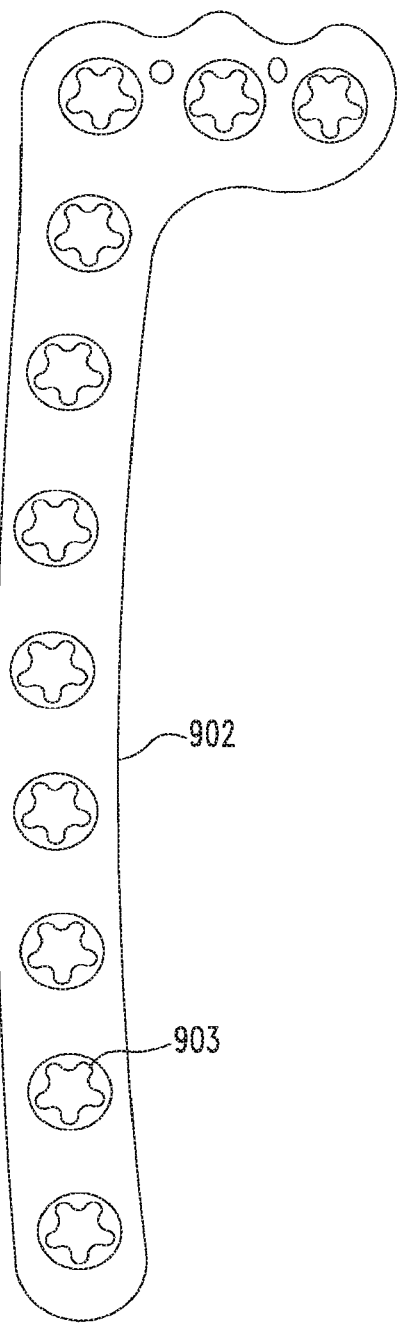

FIGS. 31 and 32 illustrate bone plates 700, 702. The bone plates may have one or more features as described above. The bone plates 900, 902 are made from a carbon fiber-reinforced composite material or a fiber-reinforced biocompatible polymer. As an example, the material may be the ENDOLIGN product available from Invibio Inc., located at 300 Conshohocken State Road, West Conshohocken, Pa. As another example, the material may be a high strength version of polyetheretherketone, commonly known as PEEK. The bone plates 900, 902 include openings 903, which may be machined or in-molded. The openings 903 may be threaded or non-threaded. Threaded openings may be partially or fully threaded and may have single or multiple leads. The openings 903 may be a hole, slot, or provisional mounting holes. The openings 903 may be reinforced. The openings 903 may include locking tabs which may engage with a locking screw.

Figure 33:
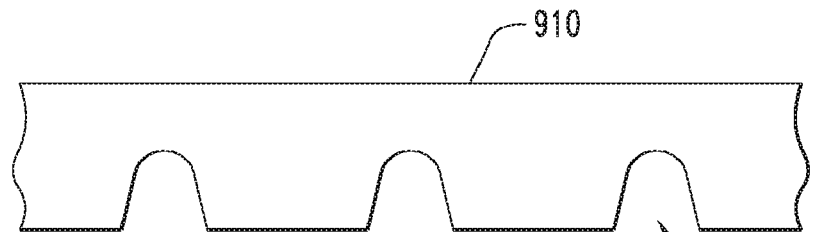
FIG. 33 illustrates a bone plate in a second embodiment.
Figure 34:
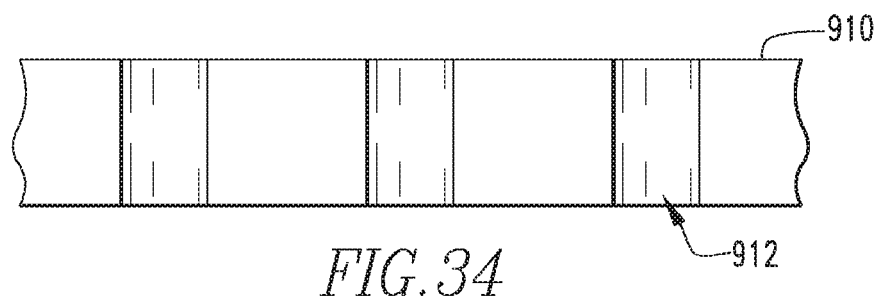
FIG. 34 is a bottom view of the embodiment shown in FIG. 33.

FIGS. 33 and 34 illustrate a bone plate 910 with one or more in-molded features 912, such as an arcuate cutout. In other words, the feature is manufactured contemporaneously with the bone plate and is not a result of a later manufacturing step.

Figure 35:
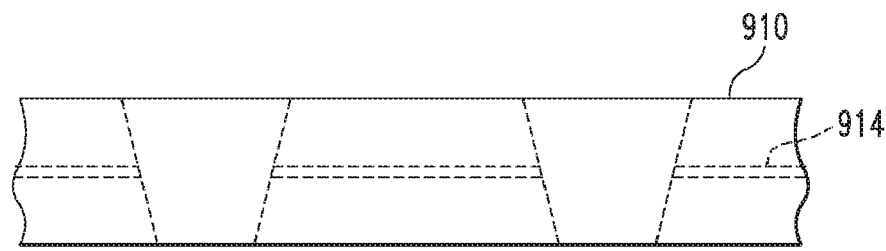
FIG. 35 illustrates a bone plate in a third embodiment.

FIG. 35 illustrates another embodiment of the bone plate 910 with one or more stiffeners or structural reinforcements 914 surrounded by a polymer or composite material. The structural reinforcements 914 may be made from any biocompatible material, such as a metal, ceramic, polymer, or a composite.

Figure 36:
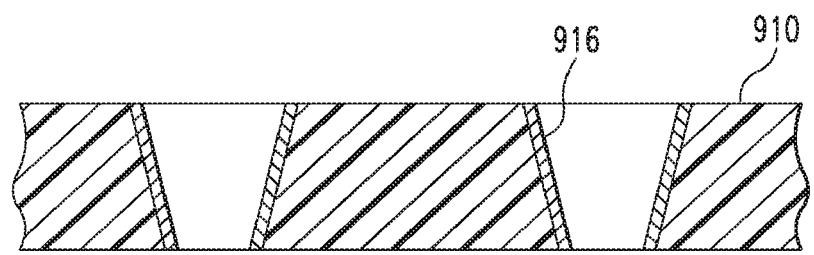
FIG. 36 illustrates a bone plate in the fourth embodiment.

FIG. 36 illustrates another embodiment of the bone plate 910 with one or more insertion elements 916. The insertion element 916 is placed relative to an opening to reinforce the opening. In some embodiments, the insertion element may be threaded. The insertion elements 916 may be made from any biocompatible material, such as a metal ceramic, polymer, or a composite.

Figure 37:
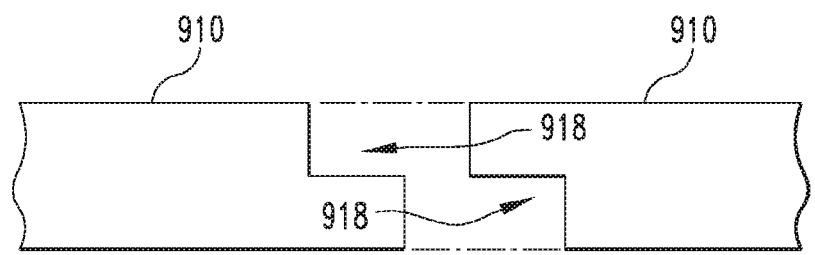
FIG. 37 illustrates a bone plate in a fifth embodiment.

FIG. 37 illustrates another embodiment of the bone plate 910. The bone plate 210 may include one or more connectors 918. The connector 918 may be used to connect one or more bone plates 910. This may allow for a patient-specific bone plate. For example, bone plates may be attached in series to obtain a particular length. U.S. Pat. No. 7,090,676 to Huebner et al. disclose a method of connecting adjacent bone plate portions. The '676 patent is herein incorporated by reference. U.S. Patent Application Publication No. 2008/0097445 A1 to Weinstein discloses another method of connecting adjacent bone plate portions. The '445 application is herein incorporated by reference.

Figure 38:
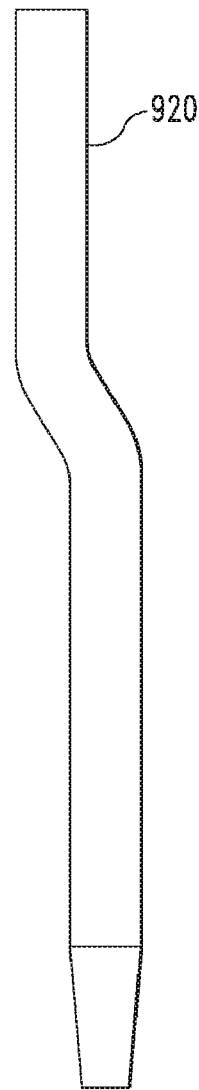
FIG. 38 illustrates a bone plate in a sixth embodiment.

FIG. 38 illustrates a patient specific bone plate 920. The shape of the bone plate 920 is adjusted intraoperatively through the application of energy to match a patient's anatomy, to provide a buttress, to compress a fracture, or to distract a fracture. A polymer material presents the advantage of intraoperatively adjusting the bone plate. In the past, bending a bone plate required a machine strong enough to bend metal. Such a machine is generally considered to be too cost prohibitive for placement in an operating room. For a polymer device, other forms of energy may be used to reshape the bone plate. As examples, such energy may be in the form of heat or acoustic energy, such as ultrasound. As an example, energy may be applied to the bone plate and then manually shaped. In one particular method, a patient's bone is analyzed to define a contour, and the bone plate is then modified relative to the contour. In some embodiments, the bone plate is modified to match the contour. In other embodiments, the bone plate is modified such that the bone plate has potential energy and imparts energy to the bone when implanted to compress or distract the bone. For example, the bone plate may be bent to provide a spring-bias when applied to the bone.

Figure 39:
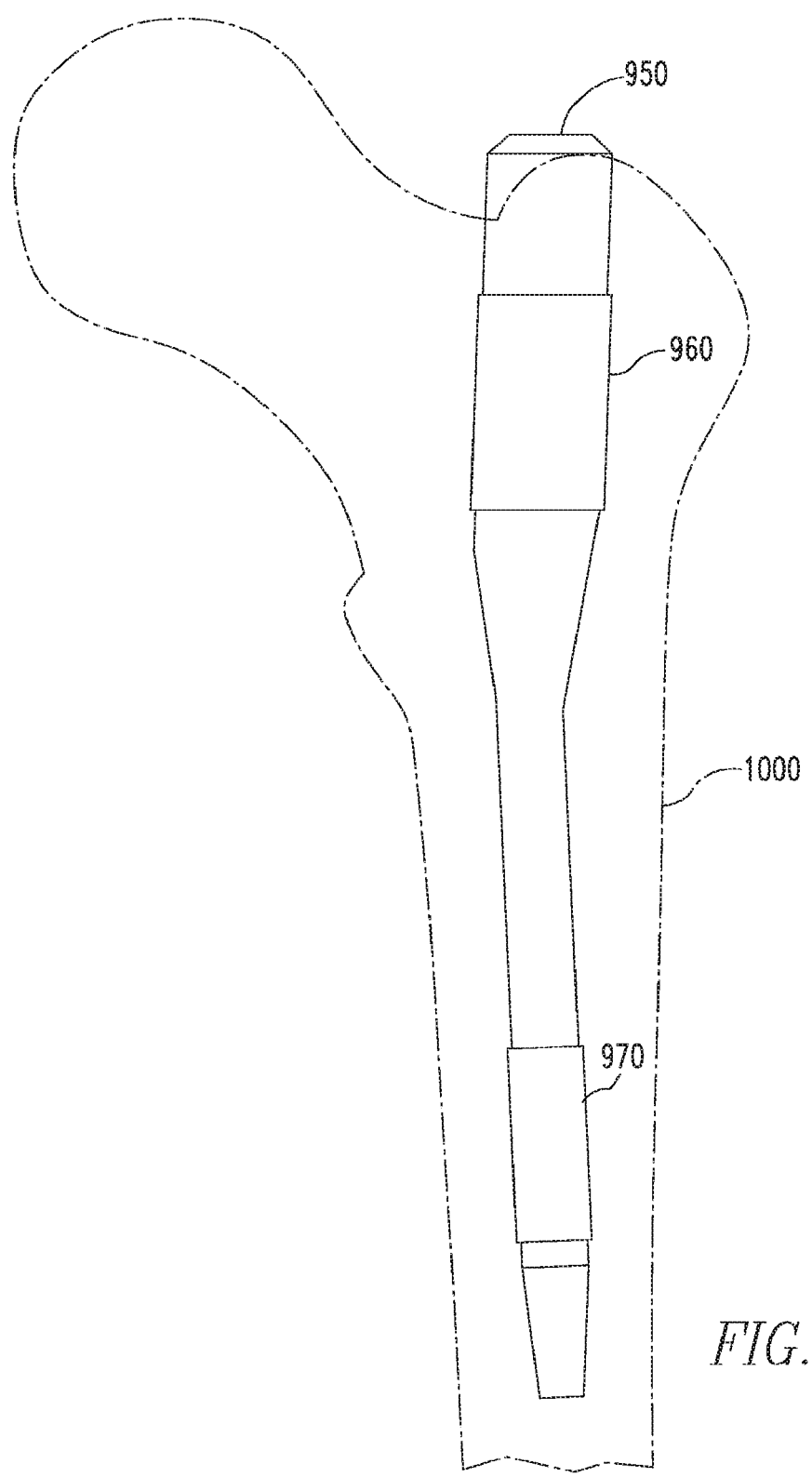
FIG. 39 illustrates the intramedullary nail in a twelfth embodiment.

FIG. 39 illustrates an intramedullary nail 950. The intramedullary nail may have one or more features as described above. In the depicted embodiment, the nail 950 is made from a polymer or a composite and is implanted in a bone 1000. The nail 950 includes one or more sleeves. In the depicted embodiment, the nail 950 includes a first sleeve 960 and a second sleeve 970, but any number of sleeves may be used. The sleeves 960, 970 are made from an abrasion resistant, biocompatible material, such as stainless steel, titanium, or ceramic. The sleeves 960, 970 may be in the form of a band or cylinder pressed onto the nail 950. The sleeves 960. 970 may incorporate through holes. For example, sleeve 970 may have through holes for locking the nail in place with a fastener.

Figure 40:
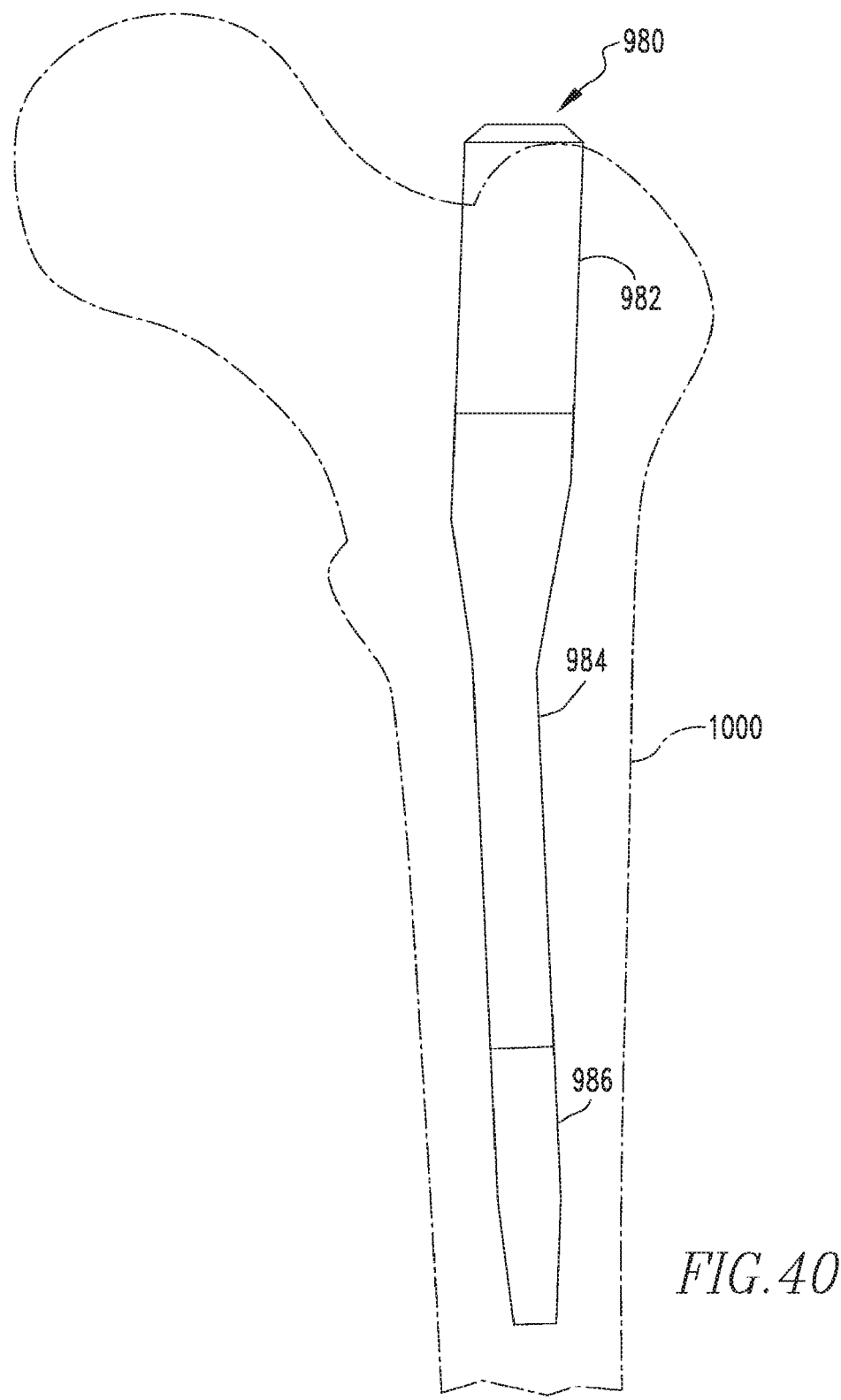
FIG. 40 illustrates the intramedullary nail in a thirteenth embodiment.

FIG. 40 illustrates an intramedullary nail 980. The nail 980 includes a proximal portion 982, a working portion 984, and a distal portion 986. The working portion 984 is made from a polymer or composite and may incorporate one or more features described above in conjunction with intramedullary nails. The proximal and distal portions 982, 986 are made from a biocompatible, abrasion resistant material. As an example, the proximal and distal portions 982, 986 may be made from stainless steel, titanium, or ceramic. The proximal portion 982 may include features, such as a slot and threaded hole, for connecting an instrument, such as an insertion handle, to the nail 980. The distal portion 986 may include a vertical slot to bifurcate a portion thereof. The proximal portion 982, the working portion 984, and the distal portion 986 may be cannulated.

The working portion 984 may be used to customize the stiffness of the construct. Further, the working portion 984 may be used to customize dimensions, such as length, inner diameter, and outer diameter. As an example, the outer diameter may be sized and dimensioned to match the bone, and the inner diameter may be selected to achieve a desired stiffness. The working portion 984 may have any number of cross-sections, including, but not limited to, cylindrical, octagonal, hexagonal, triangular, rectangular, trapezoidal, u-shaped, c-shaped, and d-shaped. Further, the working portion 984 may match a cross-section of the proximal portion 982 and transition to a cross-section of a distal portion 986, or vice versa.

The working portion 984 may be attached to the proximal or distal portion in any number of different ways. As examples, the working portion may be connected to one of the distal and proximal portions 982, 986 by ultrasonic welding, by knurling the distal and proximal portions 982, 986 and press fitting the working portion 984 thereon, by knurling the distal and proximal portions 982, 986 and molding the working portion 984 thereon, by a threaded connection, by a snap-fit connection, or by a pin connection. In one particular embodiment, the distal and proximal portions 982, 986 have a female receptacle and the working portion 984 has a male connector, or vice versa. In another embodiment, one or more pins are used to connect the working portion 984 to one of the distal and proximal portions 982, 986. The pins may be placed at different layers and/or orientations.

Additionally, text may be printed on an implant with an iron-based radio-opaque ink so that it appears on radiographs. The process used for applying the ink is the same as is used currently to apply ink to an instrument, which is through Pad Printing. The text may include the company logo, implant size, implant lot number, quality control number, Left or Right (if appropriate), and pertinent notes or warnings (e.g., "For use with Gold Guide Drop ONLY"). Further, the text may include personalized patient information, such as patient name, patient identification information, social security number, nickname, favorite sports team name, sports team mascot, or sports team expression (e.g., "GO BOILERS!" or "GEORGIA BULLDOGS.").

Another process to show text and graphical information on the implant radio-graphically may be achieved by molding thin metal sheets in or on the body of the implant. These sheets can contain the information desired and when observed under radiographs it is viewable. The information can be machined, laser etched, or chemical etched into the thin metal sheet.

In another embodiment, there is provided a bone plate with radiographic markers located at an edge or proximate to a feature, such as a hole. The radiographic markers may be used to verify a bone plate location with an imaging device. This may be of an advantage in some procedures, such as minimally invasive surgery.

The implants may be made using various methods of manufacturing, such as compression flow molding, laminate, injection molding, vacuum assist resin transfer molding, vacuum induced preform relaxation, machining of raw or semi-finished stock, 3D weaving, mandrel wound, and thermoforming. If a mandrel is used, it may be made from a single section or a multiple section.

In some embodiments, the fiber layup and/or fiber orientation may be controlled to adjust the overall strength of the implant. In some embodiment, advanced fiber placement technology may be used to control or vary the stiffness of the implant in particular locations. Typically, fiber layers are placed in 0, ±45 and 90 degree plies. However, by continuously varying fiber angles, the stiffness of particular portions of the implant can also be varied. The fiber angles may be varied as a function of the circumferential coordinate or longitudinal coordinate of a cylinder or similar object.

Further, in some embodiments, the fibers may be laid in a three dimensional weave pattern or a quasi-three dimensional weave pattern to substantially reduce the risk of delamination. The phrase "quasi-three dimensional weave pattern" refers to weaves having in-plane yarns in the adjacent layers interlocked to one another to form overall three-dimensional networks. Generally, three dimensional weaves have some yarns oriented in the thickness direction, which do not directly contribute to the in-plane strength of the composite material. These yarns may cause kinks to the in-plane yarns at points where they are inserted and may become weak points in the composites due to the high stress concentrations. Quasi-three dimensional weaves have yarns that are primarily located in the plane of the weave. The yarns are interlocked not only with the cross yarns of their own layer, but also go deeper into the weave to interlock with the yarn of the adjacent layer. Although undulations of the in-plane yarns can be clearly identified, none of the yarns is specifically oriented in the thickness direction. The contribution of the in-plane yarns to the in-plane properties, hence, can be largely preserved.

In one embodiment, a medicament containment device containing a medicament, such as for example an antibiotic, is attached to an implant. The medicament containment device can degrade upon exposure to energy, such as energy from an energy source. The implant, including the medicament containment device, is implanted or inserted into an environment such as a patient's body. An energy source can be used outside the patient's body, but in proximity to the implant, to apply energy to the medicament containment device. Upon exposure to the energy, the medicament containment device can disintegrate, degrade, or otherwise alter in structure or composition or both, partially or totally, sufficient to allow a medicament to penetrate (hereinafter "degrade") and release at least part of the medicament into the environment. As an example, the medicament can kill and/or disrupt bacterial cells or other infectious cells that form in proximity to the implant. "Medicament" as used herein may include any medicine or other composition that can be used to promote healing or recovering, such as from an infection (whether bacterial, viral, or otherwise). Examples of suitable medicament for use in connection with various embodiments includes osteoblast affecting agents, osteoclast affecting agents, antibiotics, anti-inflammatory agents, pain medication, osteogenic factors, prostaglandins, radio-markers, angiogenic factors, vasodilators, growth factors, or a combination of any of the above.

In some embodiments, all or portions of the fibers and/or the resin may be resorbable. As examples, the resin may be resorbable, the fibers may be resorbable, or a percentage (such as one-half or one-third) of fibers may be resorbable.

Typically, a fastener is used to secure the orthopaedic fixation device within or to bone. The fastener may be completed threaded or have a distal threaded end portion. However, a screw thread may disrupt a carbon-fiber reinforced polymer and produce unwanted particles. Other methods of securing the orthopaedic fixation device within or to bone include gluing the fixation device to bone, inserting a non-threaded fastener through the fixation device and gluing it to bone, inserting a non-threaded fastener through the fixation device and bone and expanding the fastener, inserting a non-threaded fastener through the fixation device and bone and ultrasonically welding the fastener to the fixation device, and inserting a non-threaded fastener through the fixation device and bone and shrinking the fixation device around the fastener.

A number of implementations have been described. Nevertheless, it will be understood that various modifications may be made without departing from the spirit and scope of the claimed invention. For example, while the fibers of each layer of the laminated composite orthopaedic fixation device of some implementations have been described as generally straight and parallel, in other implementations, the fibers within each layer may be woven, braided, or twisted into groups of fibers, which can be arranged in parallel within the layer and embedded within, or impregnated with, thermoplastic material. Furthermore, the fibers can be woven or braided to form three dimensional structures. Similarly, the fibers can be arranged to interconnect with fibers of an adjacent layer to form a three dimensional construct. Additionally, in some implementations, a composite tape can include fibers or groups of fibers woven or braided into a narrow sheet, where the width of the sheet is approximately equal to the width of the tape. The fibers can then be embedded within, or impregnated with, thermoplastic material. Similarly, the fibers of one or more layer may be discontinuous, such as chopped fibers. In some implementations, a layer of thermoplastic material without fibers can be included between one or more of the fiber reinforced composite layers.

In some implementations, the composite material can also include different polyketone materials, such as Polyaryletherketone (PAEK), or other biocompatible thermoplastic materials. Similarly, other groups of biocompatible materials that are non-hygroscopic, or otherwise maintain structural characteristics, can be used.

In some implementations, the nail 100 can include features to provide additional benefits such as reduction of debris released into the body that can result from contact between the nail 100 and other implants and/or instruments during or after the implantation. For example, the nail 100 may be formed without any apertures 111 in each of the first section 101 and the second section 103. The nail 100 can include projections such as hook-shaped members or claws on the first section 101 and/or second section 103 for engaging the nail 100 to the inner cortical walls of the bone canal. The projections can be an integral part or separate entities to the nail 100. In some implementations, the nail 100 is inserted in the bone while the projections are retracted and later expanded for engagement with the cortical walls. In other implementations, the nail 100 can include apertures having metal or thermoplastic inserts, bushings, or sleeves to reduce or eliminate contact between a fastener and carbon fibers. Additionally, the nail 100 may have threaded or non-threaded apertures 111 where the pin P or other fastener, can be secured via biocompatible adhesive, ultrasonic welding, or a shape memory screw and/or insert.

Additionally, though the nail 100 has been described as including a single medial portion 100c, two or more separate portions may be included, where each portion is formed from multiple layers of a fiber-reinforced composite material, and the portions may have different circumference dimensions. Additionally, the listing of designs in table one is not an exhaustive list, and other designs can be included in the library of designs 430 and the nail 100 or other orthopaedic fixation device can have other designs. Accordingly, other embodiments are within the scope of the following claims.

The invention claimed is:

1. An intramedullary (IM) nail comprising:
   a longitudinal axis;
   a head portion;
   a shaft portion;
   a transition region between the head portion and the shaft portion;
   at least one aperture for receiving a fastener; and
   a plurality of radio-opaque markers including first, second, third and fourth radio-opaque markers, the first, second, third and fourth radio-opaque markers being positioned adjacent to the at least one aperture, the first, second, third, and fourth radio-opaque markers being adapted and configured so that, in use, the first, second, third, and fourth radio-opaque markers are capable of illustrating when an imaging device is properly aligned with the at least one aperture;
   wherein the IM nail includes a plurality of layers, each layer of the plurality of layers including a thermoplastic component and a fiber component, each layer of the plurality of layers having a selected fiber angle pattern;
   wherein the plurality of layers include at least a first layer, a second layer, and a third layer, the second layer being wrapped about the first layer so that the second layer has a different fiber angle pattern than the first layer, and the third layer is wrapped about the second layer so that the third layer has a different fiber angle pattern than the second layer.

2. The IM nail of claim 1, wherein, for each layer of the plurality of layers, the fibers are orientated generally parallel with respect to a longitudinal axis of that layer.

3. The IM nail of claim 1, further comprising an embedded electronic component.

4. The IM nail of claim 1, wherein selected fiber angle patterns of the layers are selected such that the IM nail exhibits a selected stiffness characteristic.

5. The IM nail of claim 1, further comprising an exterior coating of a thermoplastic material with substantially no fiber component.

6. The IM nail of claim 5, wherein the exterior coating comprises a layer in the form of a tape or tow.

7. The IM nail-of claim 1, wherein the head portion comprises a greater number of layers than a number of layers of the shaft portion.

8. The IM nail of claim 1, wherein the at least one aperture includes a first aperture and a second aperture, the first aperture being located within the shaft portion, the second aperture being located within the head portion, the first aperture including the first, second, third, and fourth radio-opaque markers, the second aperture including first, second, third and fourth radio-opaque markers, the first, second, third and fourth radio-opaque markers of the second aperture being positioned adjacent to the second aperture, the first, second, third, and fourth radio-opaque markers of the second aperture being adapted and configured so that, in use, the first, second, third, and fourth radio-opaque markers of the second aperture are capable of illustrating when an imaging device is properly aligned with the second aperture.

9. The IM nail of claim 8, further comprising a sensor spaced apart from each of the first and second apertures.

10. The IM nail of claim 8, further comprising a sleeve disposed in each of the first and second apertures, the sleeves being configured to receive the fasteners therein.

11. The IM nail of claim 8, wherein the fibers of each layer are routed around the first and second apertures.

12. The IM nail of claim 1, wherein each layer of the plurality of layers is constructed from a continuous fiber-reinforced material, the continuous fiber-reinforced material having a length and a width, each fiber of the continuous fiber-reinforced material being generally aligned in parallel with the length of the continuous fiber-reinforced material.

13. The IM nail of claim 1, wherein the second layer is wrapped about the first layer such that the longitudinal axis of the fibers of the second layer are oriented at approximately a forty-five degree angle with respect to the longitudinal axis of the IM nail, and the third layer is wrapped about the second layer such that the longitudinal axis of the fibers of the third layer are oriented at approximately a negative forty-five degree angle with respect to the longitudinal axis of the IM nail.

14. The IM nail of claim 13, wherein the first layer of the IM nail is wrapped generally perpendicular to the longitudinal axis of the IM nail.

15. The IM nail of claim 13, further comprising a fourth layer wrapped about the third layer, the fourth layer being wrapped about the third layer so that the fourth layer has a different fiber angle pattern than the third layer.

16. The IM nail of claim 15, wherein the fibers of the fourth layer are oriented generally parallel to the longitudinal axis of the IM nail.

17. The IM nail of claim 1, wherein the head portion has a first circumference, the shaft portion has a second circumference, the second circumference being smaller than the first circumference, the transition region having a decreasing circumference along the longitudinal axis from the first circumference.

18. The IM nail of claim 1, wherein the IM nail includes a solid central core.

19. The IM Nail of claim 1, wherein in use, the first and second radio-opaque markers are capable of being aligned with respect to each other and the third and fourth radio-opaque markers are capable of being aligned with respect to each other when an imaging device is properly aligned with the at least one aperture.

20. An intramedullary (IM) nail for implantation within an intramedullary canal of a long bone, the IM nail comprising:
    a body portion having a longitudinal axis, the body portion including at least one aperture for receiving a fastener and first, second, third and fourth radio-opaque markers embedded within the body portion of the IM nail, the first, second, third and fourth radio-opaque-markers positioned adjacent to the at least one aperture, the first, second, third, and fourth radio-opaque markers being adapted and configured so that, in use, the first and second radio-opaque markers are capable of being aligned with respect to each other and the third and fourth radio-opaque markers are capable of being aligned with respect to each other when an imaging device is properly aligned with the at least one aperture;

wherein the body portion includes a plurality of layers, each layer of the plurality of layers being constructed of a composite material including a thermoplastic component and a fiber component;

wherein the plurality of layers include at least a first layer, a second layer, and a third layer, the second layer being wrapped about the first layer such that a longitudinal axis of the fibers of the second layer are oriented at a select angle with respect to the longitudinal axis of the body portion of the IM nail, and the third layer is wrapped about the second layer such that a longitudinal axis of the fibers of the third layer are oriented at a select angle with respect to the longitudinal axis of the body portion of the IM nail;

wherein the select angle is one of approximately a five to a forty-five degree angle, or approximately a negative five to forty-five degree angle.

\* \* \* \* \*